United States Patent [19]

Garber

[11] Patent Number: 5,065,444

[45] Date of Patent: Nov. 12, 1991

[54] STREAK REMOVAL FILTERING METHOD AND APPARATUS

[75] Inventor: David D. Garber, Cypress, Calif.

[73] Assignee: Northrop Corporation, Hawthorne, Calif.

[21] Appl. No.: 642,133

[22] Filed: Jan. 15, 1991

Related U.S. Application Data

[63] Continuation of Ser. No. 153,854, Feb. 8, 1988, abandoned, which is a continuation-in-part of Ser. No. 77,717, Jul. 24, 1987, abandoned.

[51] Int. Cl.$^5$ .............................................. G06K 9/40
[52] U.S. Cl. ....................................... 382/54; 382/32; 382/51
[58] Field of Search ................... 382/30–34, 382/42, 51, 54; 358/166, 167

[56] References Cited

U.S. PATENT DOCUMENTS

| | | | |
|---|---|---|---|
| 4,695,884 | 9/1987 | Anastassiou et al. | 382/51 |
| 4,742,551 | 5/1988 | Deering | 382/51 |
| 4,809,344 | 2/1989 | Peppers et al. | 382/32 |
| 4,866,785 | 9/1989 | Shibano | 382/51 |

Primary Examiner—David K. Moore
Assistant Examiner—Jose L. Couso
Attorney, Agent, or Firm—Terry J. Anderson; Robert B. Block

[57] ABSTRACT

A filter for decreasing sensor artifacts in an image frame as, for instance, sensor induced streaking in the image frame, has a frame buffer for temporary storing the picture elements of the image frame. A picture element mask is utilized to group related picture elements and statistics are collected with respect to these grouped picture elements. Correction parameters are determined utilizing these statistics and these are then utilized to correct the individual picture elements to remove the sensory induced artifacts. The statistics can be collected with respect to picture element gain and picture element offset with the correction parameters then determined utilizing the picture element gain and picture element offset.

10 Claims, 11 Drawing Sheets

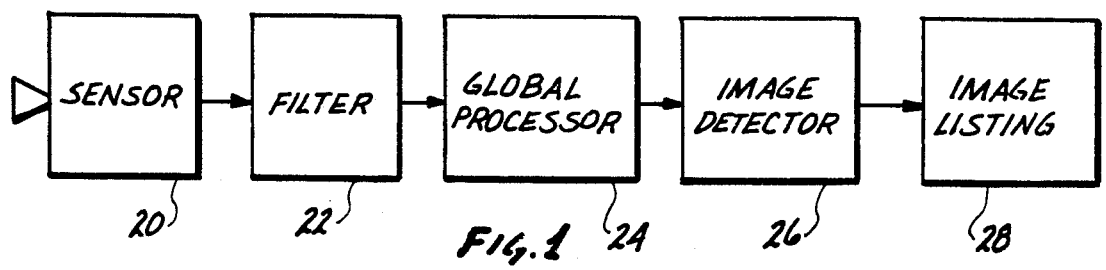
Fig. 1
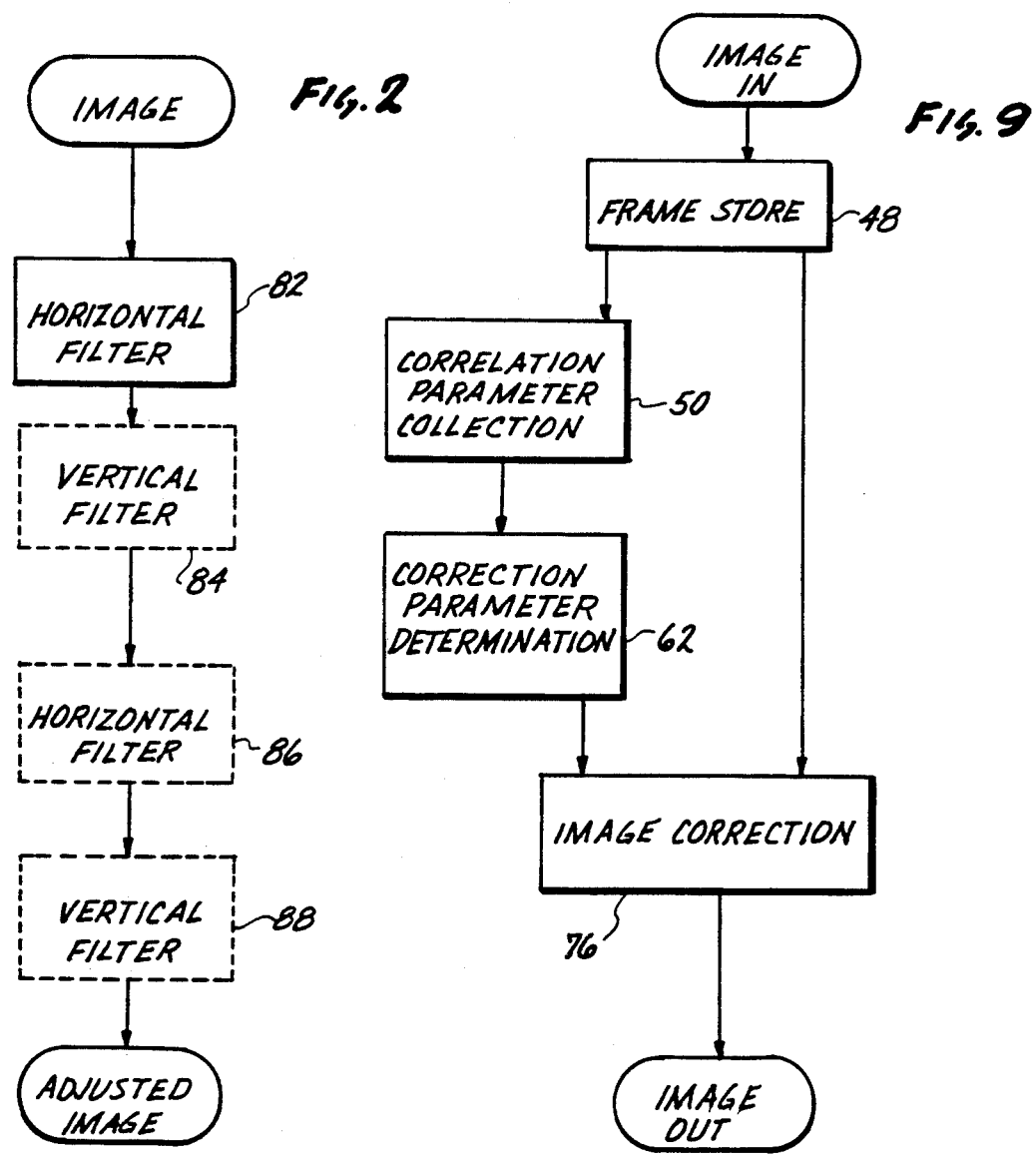
Fig. 2
Fig. 9

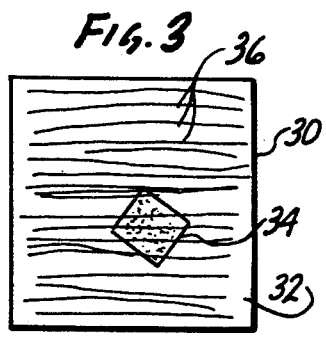
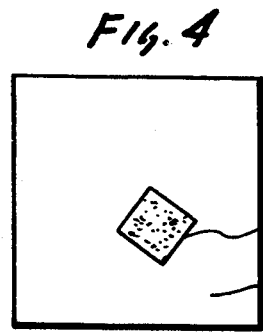
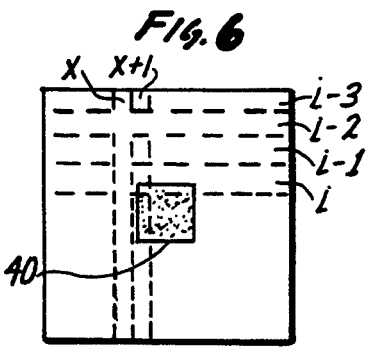
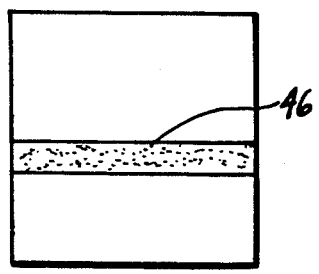
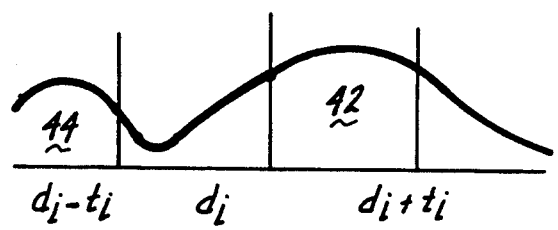
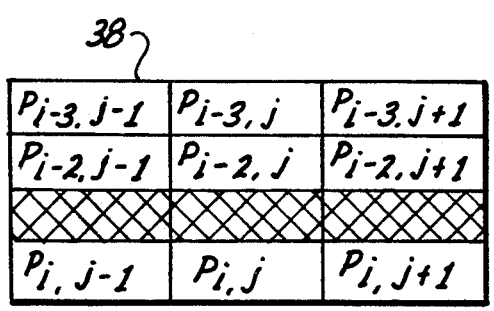
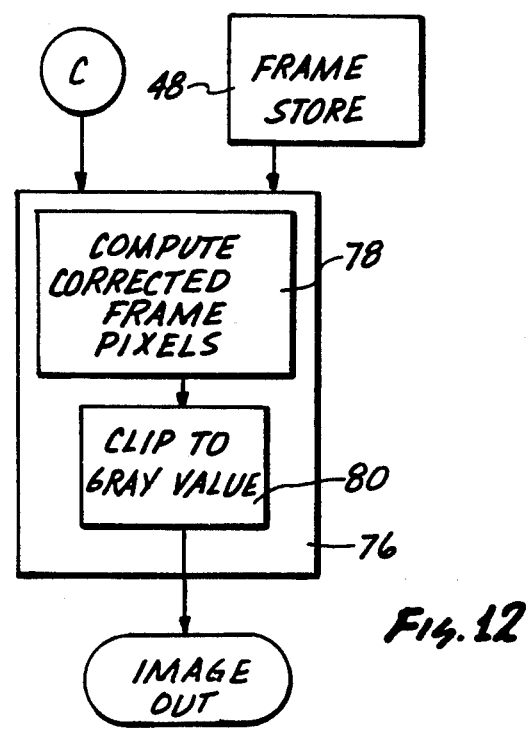

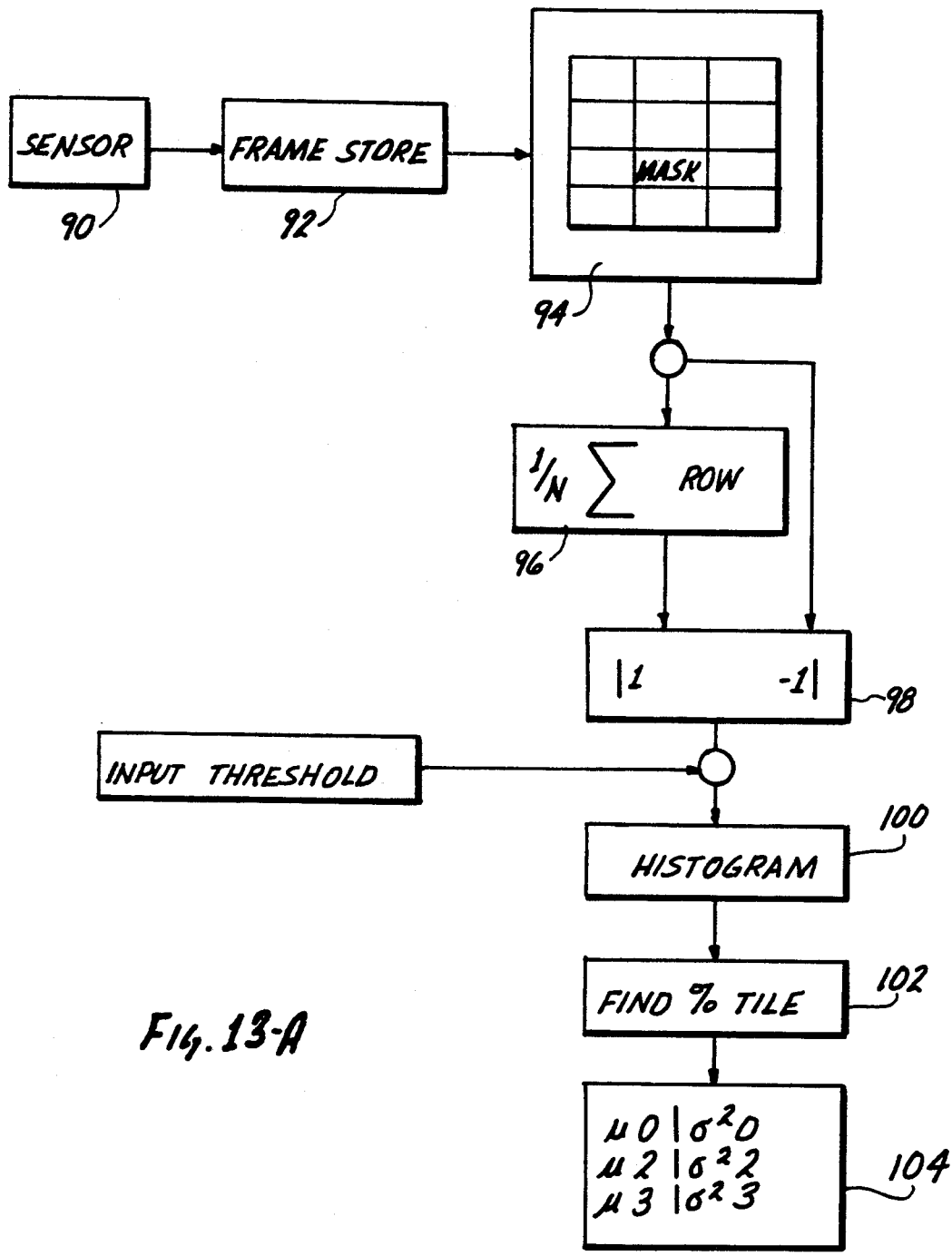
FIG. 13-A

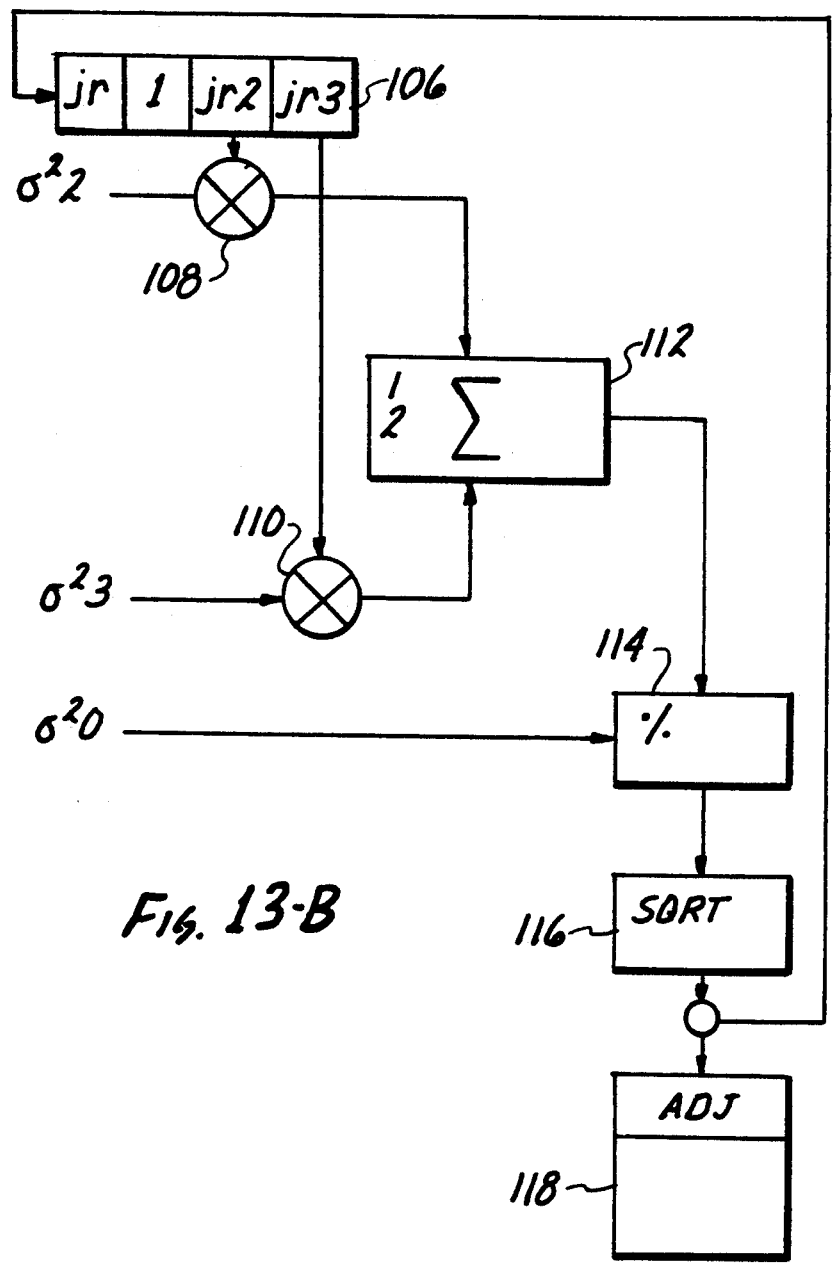
Fig. 13-B

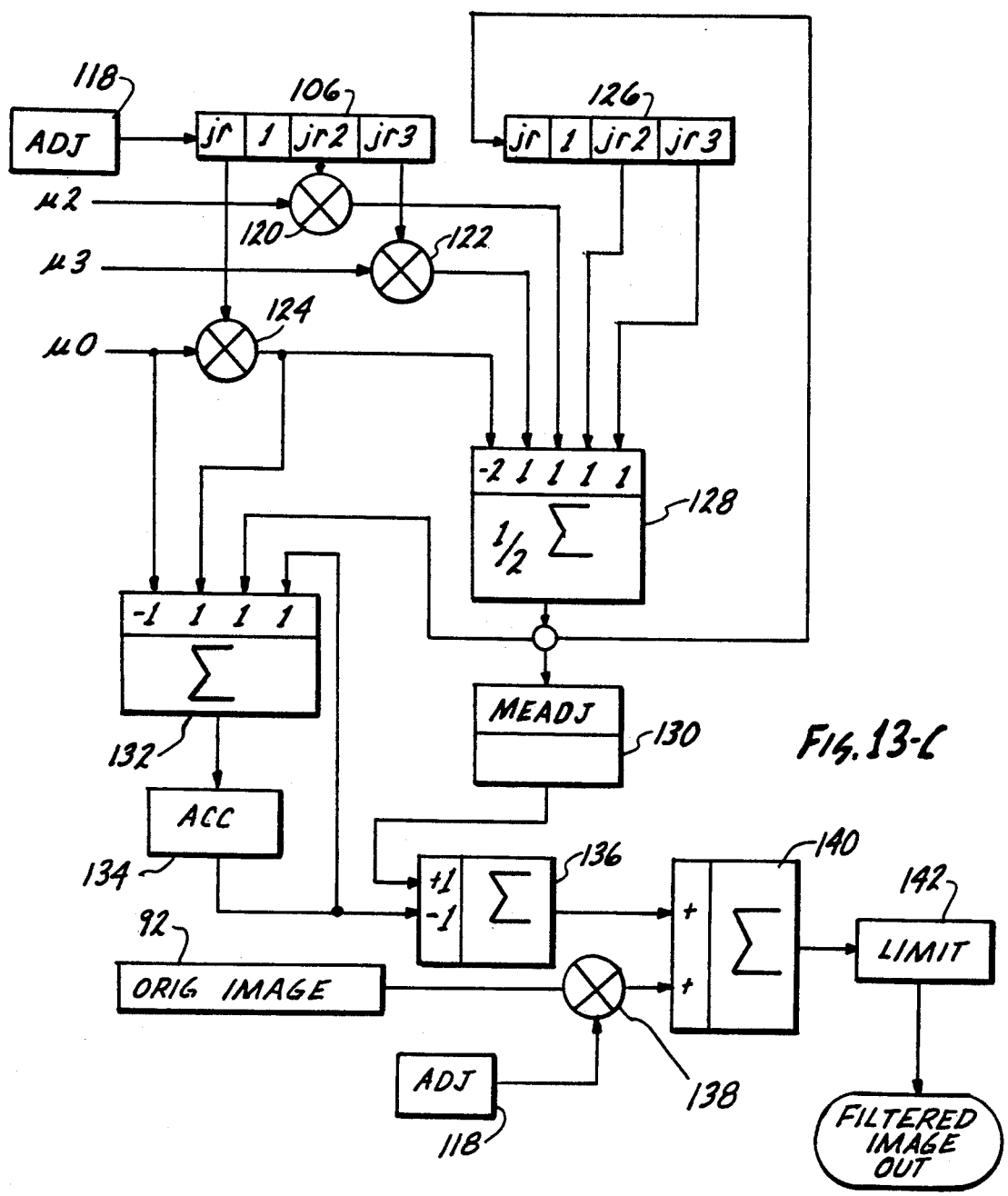
FIG. 13-C

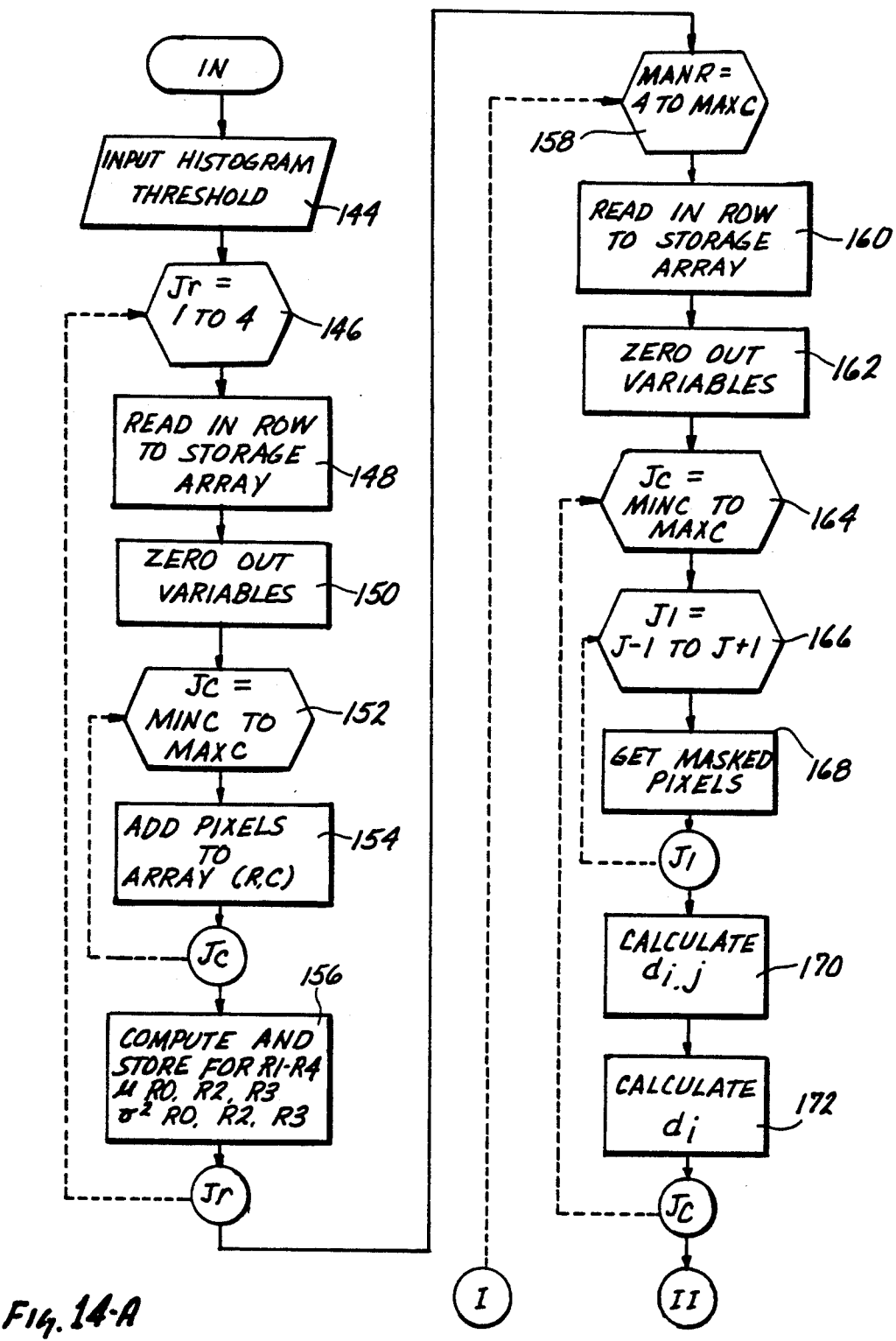
Fig. 14-A

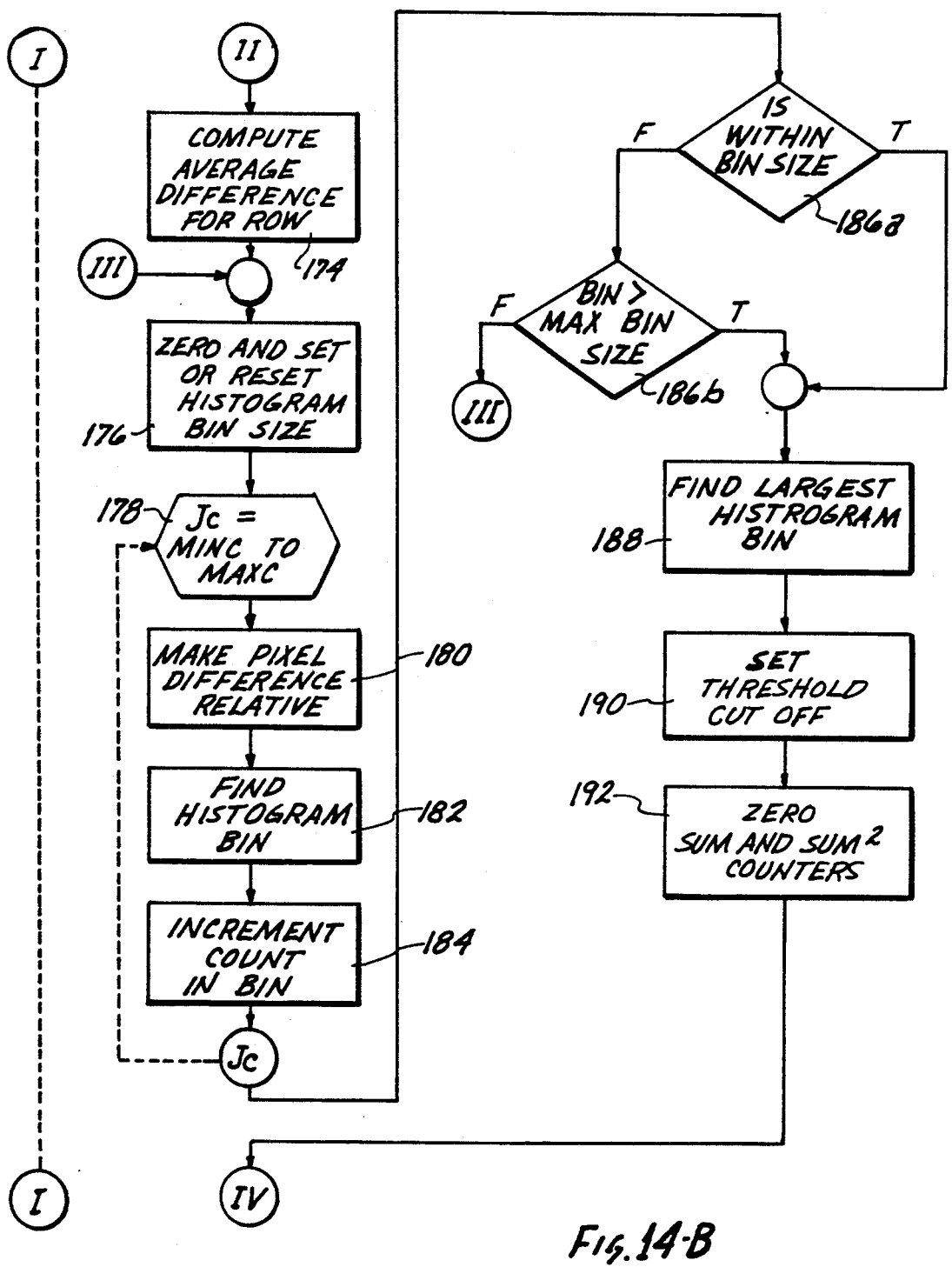
Fig. 14-B

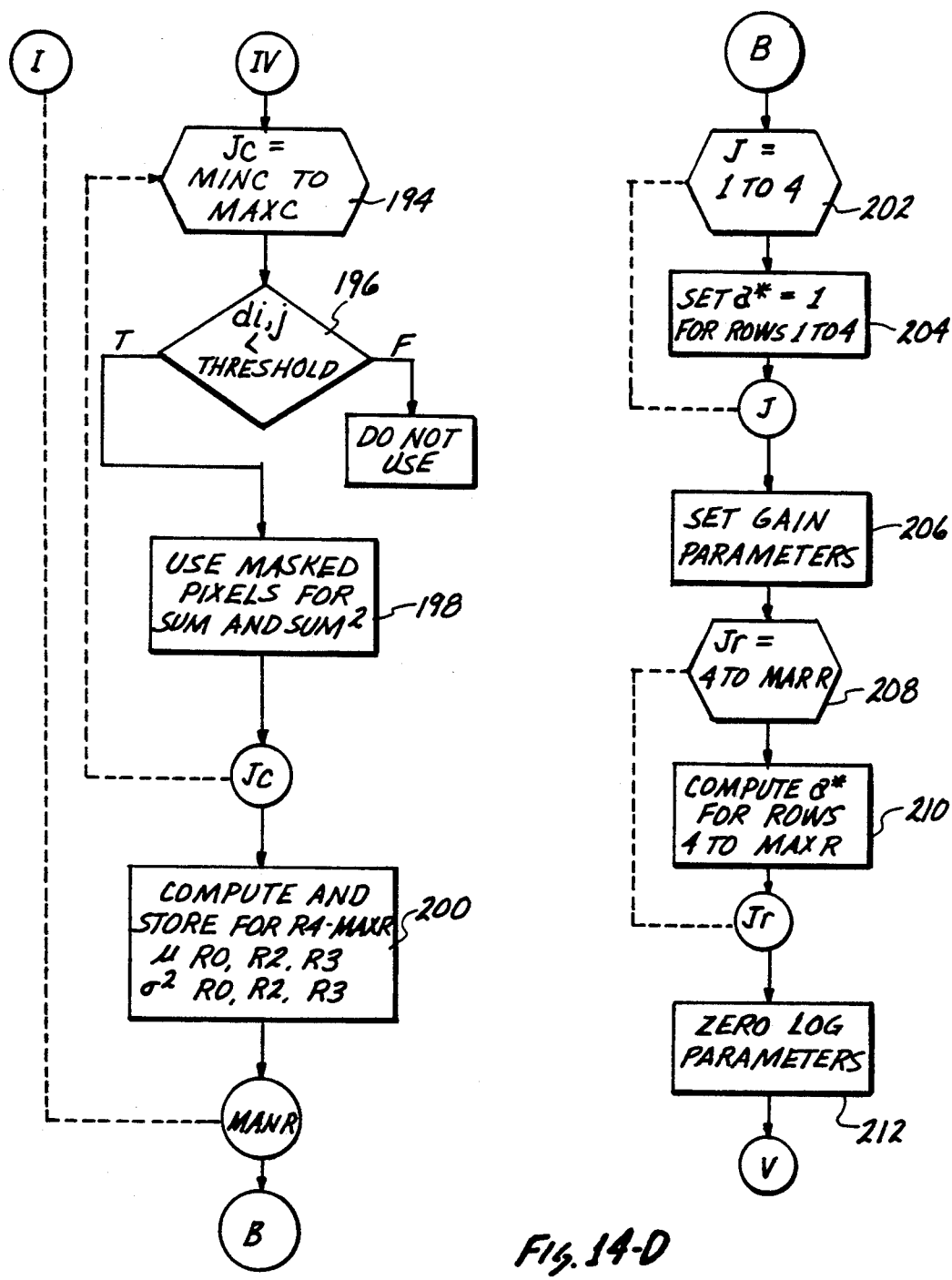

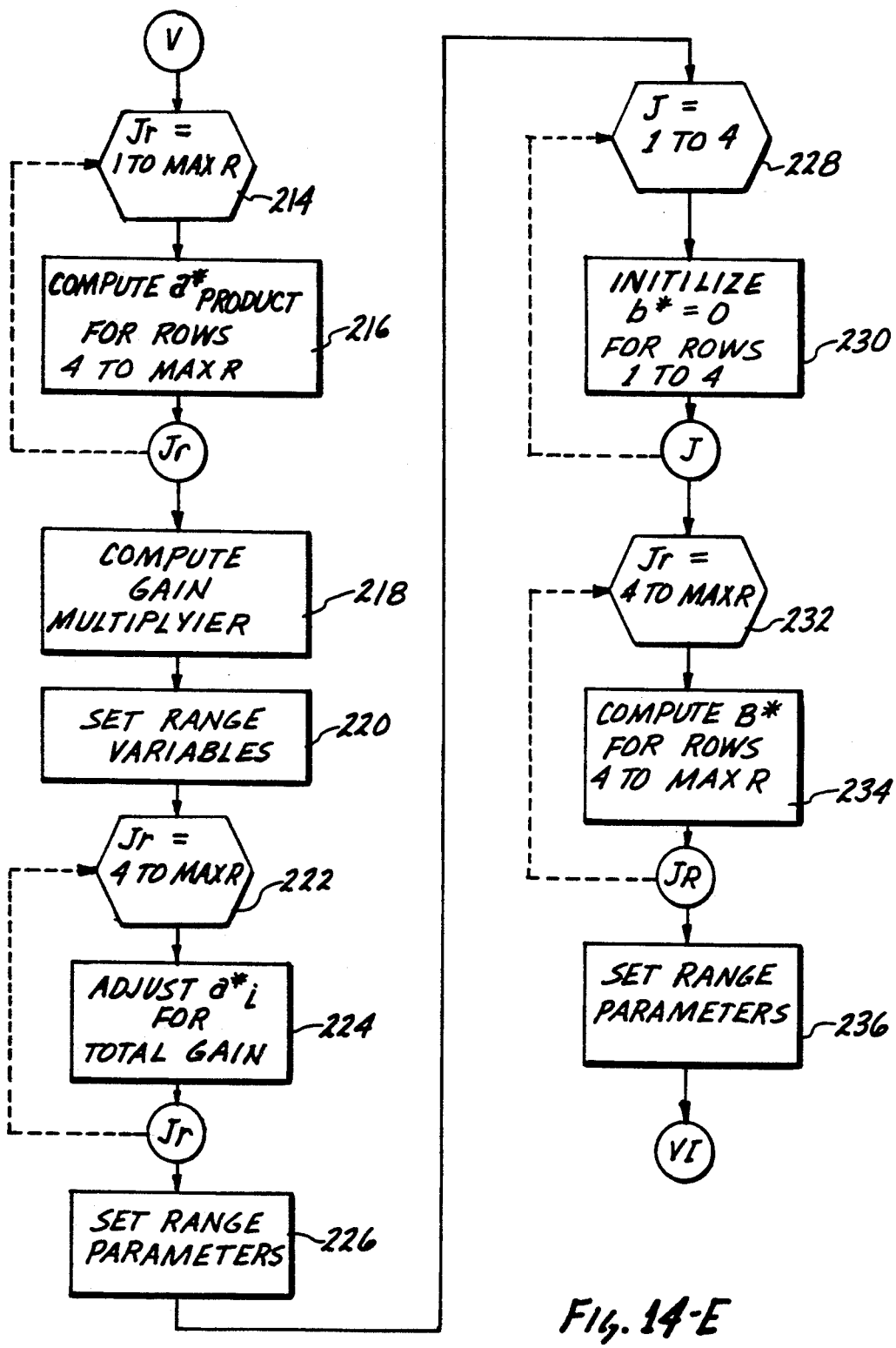
Fig. 14-E

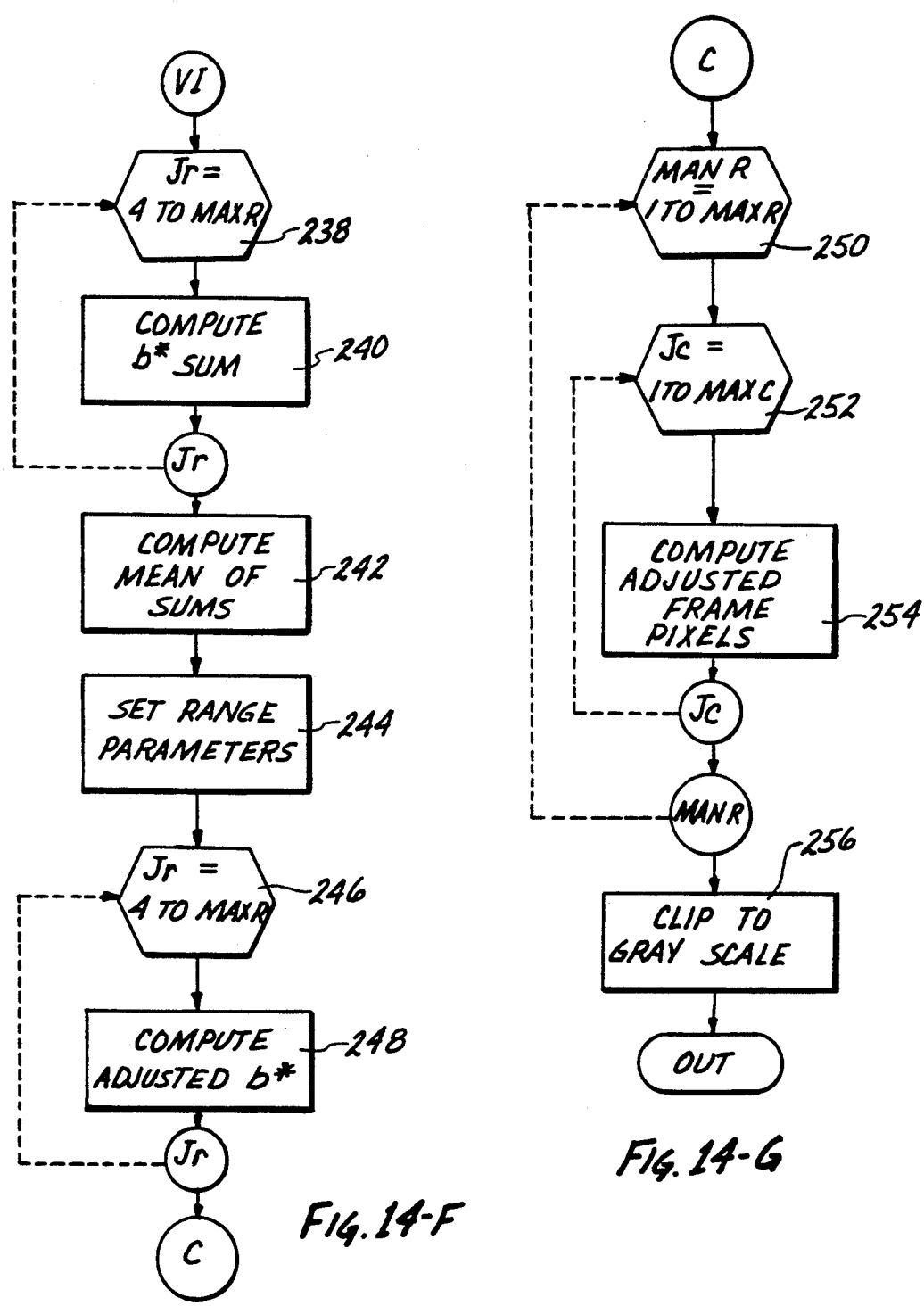
Fig. 14-F
Fig. 14-G

STREAK REMOVAL FILTERING METHOD AND APPARATUS

CONTRACTUAL ORIGIN OF THE INVENTION

The United States government has rights in this invention pursuant to Contract No. DAAH01-82-C-A106.

CROSS REFERENCE TO RELATED APPLICATIONS

This is a continuation of copending application Ser. No. 07/153,854 filed on Feb. 8, 1988, now abandoned which application is filed as a continuation in part of an application entitled TARGET ACQUISITION AND TRACKING SYSTEM, Ser. No. 077,717, filed in the name of James J. Reis, Anthony L. Luk, Antonio B. Lucero, and David D. Garber on July 24, 1987, the entire contents of which are herein incorporated by reference.

BACKGROUND OF INVENTION

This invention is directed to an apparatus and method for processing image frames to decrease sensor artifacts in the image frames, more particularly to decrease sensor streaking artifacts in the image frames.

Many sensors for collecting data have anomalies in the sensors which cause artifacts in images output by the sensors. Typical of sensors which exhibit these properties are infrared sensors, i.e. IR sensors. Multi-detector parallel scanning IR sensors (including common module FLIR sensors and focal plane arrays) can induce sensory artifacts such as streaking into the image output of these sensors. The sensor artifacts degrade the performance of other downstream systems which utilize the output of the sensors.

The artifacts produced by the sensors are of varying origins. Artifacts are very noticeable for IR sensors during 'warming up' of the sensors. However, individual elements in a multiple element sensor also change or drift over short periods of time even after the sensor is in a full operational mode. Additionally, response characteristics of individual sensor elements are also dependent upon the content of the scene which the sensor is detecting. For IR sensors very hot objects as, for instance, burning objects, engine compartments of vehicles, exhaust areas of vehicles and the like cause excessive streaking artifacts in data images obtained utilizing the IR sensor.

Temporal induced artifacts and hot spot induced artifacts are very difficult to remove utilizing filters which rely on measuring sensor response or filters which rely on the use of a large set of natural images or uniform test images. Artifacts would also degrade the effectiveness of time averaging filters which might utilize a large sequence of images over time to produce an optimal streak removal filter. Further, this last type of filter would require considerable computational requirements and image storage requirements for the production and storage of a sufficiently large number of images to serve as a basis for the filter. Also, by requiring the use of many sequential images for filtering purposes the ability to operate in real time or near real time is substantially compromised.

For a scanning sensor or a multiple element sensor, in theory it would be possible to have automatic gain circuits or other control circuits for each of the sensor elements and to adjust the circuits such that the output of every sensor element or sensor scan is equivalent. This, however, is not a practical solution because of the hardware demands and/or the inability of hardware or human operator to adjust the output of each sensor element or sensor scan to be totally equivalent to the output of all others.

BRIEF DESCRIPTION OF THE INVENTION

In view of the above it is evident that there exists a need for new and improved filters for the removal of sensor induced artifacts from the output of sensors. Further, there exists a need for real or near real time operating filters for reducing sensor induced artifacts.

It is a broad object of this invention to provide for image filters for decreasing sensory artifacts in the output of sensors. It is a further object of this invention to provide for image filters which operate in real or near real time to decrease such sensory induced artifacts. It is an additional object of this invention to provide filters which are capable of decreasing sensory artifacts in an image frame without utilizing either prior image frames or post image frames in order to operate on a current image frame.

These and other objects as will be evident from the remainder of this specification are achieved in a filter device for decreasing sensory artifacts in an image frame which includes a frame buffer means for temporarily storing the picture elements of an image frame. The device further includes a collection means for collecting correlation parameters between related picture elements in the frame and a correction parameter determination means for determining picture element correction parameters utilizing the correlation parameters. Additionally, it includes an image correction means which utilizes the picture element correction parameters for adjusting the stored picture elements of the image frame to decrease the sensory artifacts in the image frame.

The above described filter advantageously can include a picture element mask means for grouping related picture elements during the collection of the correlating parameters. Further, the collection means advantageously can include a statistics collection means for collecting statistical parameters between related picture elements. The collection means can further advantageously include a relationship sensing means for determining a relationship of a parameter of a selected picture element with a parameter of at least a further picture element.

The relationship sensing means can advantageously include a threshold clipping means for setting a difference threshold between picture element parameters and selectively categorizing picture element parameters according to this difference threshold. Illustrative of the threshold clipping means is an histograms means for storing picture elements in a histogram and categorizing the picture element parameters in accordance with a clipping threshold established in the histogram.

The correction parameter determination means advantageously includes a picture element gain determining means for determining the differences in image frame gain between related picture elements and for generating a gain correction parameter for these related picture elements and further a picture element offset determining means for determining the difference in image frame offset between related picture elements and for generating an offset correction parameter for these related picture elements.

The objects of the invention are also achieved in a method of decreasing sensory artifacts in an image frame which includes grouping related picture elements of the image frame into sets and then collecting correlational parameters based on relationships between the members of the sets. The method further includes generating picture element correction parameters utilizing these correlational parameters and then adjusting the picture elements in the image frame with the correction parameters to decrease sensory artifacts in the image frame.

The correlational parameters can advantageously be chosen as statistical parameters as, for instance, statistical means and statistical variances. The grouping of related picture elements is advantageously achieved utilizing a picture element mask where the mask selects picture elements which are located in physical proximity with each other in an image frame. The mask can be advantageously moved across the totality of the image frame to collect the correlational parameters for use in generating the picture element correction parameters. In generating the correctional parameters, gain and offset correctional parameters between rows and columns of the picture element in the image frame can be utilized for adjusting the picture element within individual rows or columns for correcting the sensory artifacts in the image frame.

BRIEF DESCRIPTION OF THE DRAWING

This invention as described in this specification will be better understood when taken in conjunction with the drawings wherein:

FIG. 1 shows a representational view of a typical image sensor, a filter of the invention and further processors and detectors which utilize an image generated by the sensor, FIG. 2 is a schematic view in partial phantom line showing progression of an image through multiple filters constructed according to the teachings of the invention, FIG. 3 is a representational view of a typical unfiltered image output by the sensor of FIG. 1, FIG. 4 is a representational view of the same image of FIG. 3 after it has been processed by a filter of the invention, FIG. 5 is a schematic view of a typical mask utilized within a filter of the invention, FIG. 6 is a representational view of an enlarged section of an image frame similar to those of FIGS. 3 and 4, FIG. 7 is a representational view of an image frame containing a large real object in the frame which crosses the frame in essentially a horizontal direction, FIG. 8 is a diagram of a histogram related to the image frame of FIG. 6, FIG. 9 is a schematic flow diagram of certain of the steps involved in processes of the invention, FIGS. 10, 11 and 12 are schematic flow diagrams of portions of the schematic flow diagram of FIG. 9 further detailing individual portions of the schematic flow diagram of FIG. 9, FIGS. 13A-13C, taken together, comprise a schematic diagram of device implementing a filter of the invention, and FIGS. 14A-14G, taken together, comprise a detailed flow diagram of an implementation of the invention.

DETAILED DESCRIPTION OF THE INVENTION

Figure 10:
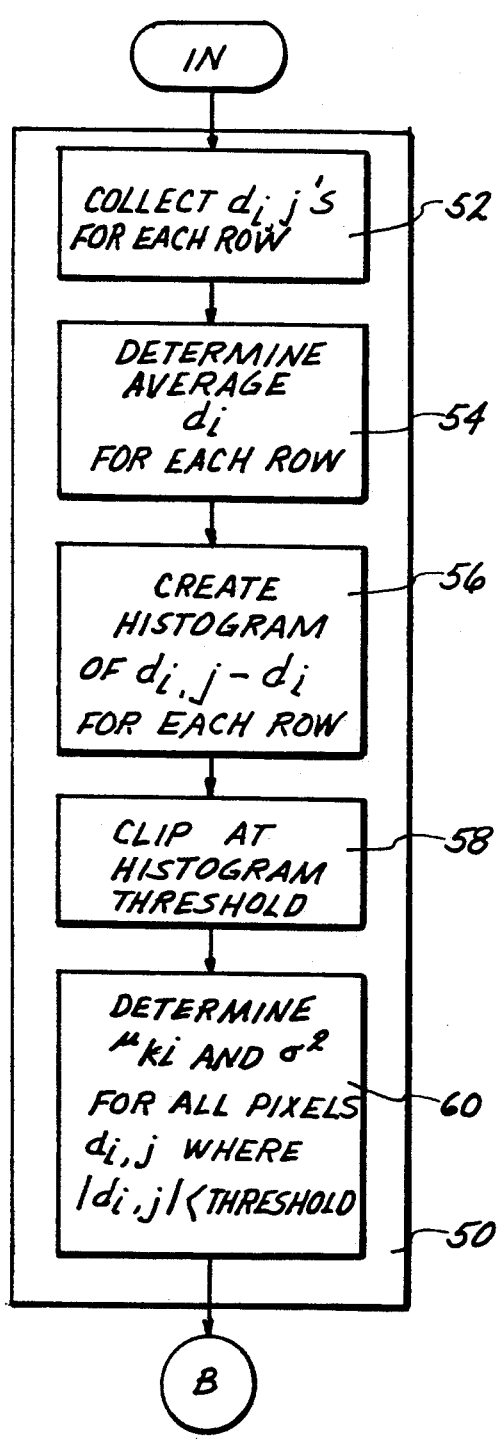

FIG. 1 shows a typical utilization of a filter of the invention. As is shown in FIG. 1, a filter of this invention is utilized in conjunction with other elements as, for instance, elements which are disclosed and described in detail in application Ser. No. 007,717 filed July 24, 1987 and entitled TARGET ACQUISITION AND TRACKING SYSTEM, the entire contents of which are herein incorporated by reference and of which this application is filed as a continuation-in-part application thereof.

In the application 'TARGET ACQUISITION AND TRACKING SYSTEM' a sensor is utilized for obtaining raw input data. This data is digitized in the sensor and then output by the sensor. Alternately analog data from a sensor can be digitized in an independent A to D converter. In any event the digitized sensor data is processed via several global processors and the output of the global processors are utilized in an image detection system for detecting target images in a target field. These target images are then output as a listing of potential targets. As is evident from the very nature of such a system, to be meaningful, image processing must be done in real or near real time.

For the target acquisition system of FIG. 1, a sensor 20 is utilized. The sensor 20 includes an appropriate sensing element therein as, for instance, a scanning IR sensor which is responsive to targets within a target field in the environment which is being scanned. The sensor 20 further includes an internal A to D (analog to digital) converter for digitizing the analog output of its sensing elements and outputing a serial stream of this raw digitized data.

In accordance with this invention the digitized serial data stream output by the sensor 20 is fed to a filter 22 of the invention. The filter 22 of the invention is utilized to remove certain sensor induced artifacts in the data output by the sensor 20. After processing by the filter 22, output from the filter 22 is fed to a global processor 24 and from there to an image detector 26. The global processor 24 processes the digitized data it receives such that the image detector 26 is capable of detecting images within a target field utilizing a variety of parameters as are more fully discussed in the above referred to application entitled TARGET ACQUISITION AND TRACKING SYSTEM. Targets detected by the image detector 26 are then processed by a target lister 28 and are separated and individually acted upon as per other teachings of the above referred to application entitled TARGET ACQUISITION AND TRACKING SYSTEM.

FIG. 3 shows a typical image frame 30 as it would exist without the use of the filter 22 of the invention. As is seen in FIG. 3, within a target field generally depicted by the numeral 32 there is a target 34. In addition to the target 34 there are a plurality of anomalous horizontal sensor induced streaks collectively identified by the numeral 35. It is evident from FIG. 3 that the horizontal streaks 36 generally degrade the totality of the image within the target field 32 and contribute to pixel clutter within the image field. Without the filter 22 of this invention, the global processor 24 and image detector 26 must contend with this pixel clutter while they are processing the image data for identification of the target 34 within the target field 32.

In a similar manner, if the sensor 20 was utilized as, for instance as a night vision sensor, a field of view presented to an observer thereof would be similarly contaminated with the horizontal streaks 36. For the purposes of FIG. 3 the sensor 20 was chosen as a horizontally scanning sensor and as a result thereof artifacts induced into the image field by the sensor 20 are expressed as the horizontal streaks 36. If a vertical scanning sensor was utilized vertical streaking would be present. In any event, the anomalous sensor induced artifacts, i.e. the streaking, degrade the unfiltered sensor image and make target acquisition or other processing of the image frame more complex and less reliable.

FIG. 4 shows the same image as is depicted in FIG. 3 with the exception that the filter 22 of the invention has been utilized to remove anomalous sensor induced horizontal streaking. In FIG. 4 the same target 34 is more clearly seen within the same target field 32 when compared to FIG. 3. It is evident in comparing FIGS. 3 and 4 that any subsequent processing of the target field 32 and the target 34 therein can be more readily done with the image of FIG. 4 because the sensor induced artifacts have been removed.

Further, the image of FIG. 4 has been processed in real or near real time by the filter 22 allowing it to be used by other real or near rear time systems as, for instance, as a night vision device or digitized image frames on a target identification device or the like.

The filter 22 of the invention operates by taking serialized digital data of an individual image frame and processes that data utilizing only the information in that individual image frame to remove anomalies from the frame which have been introduced into the frame as sensory artifacts. The filter 22 of the invention does not require prior frames or subsequent frames in order to process the data content within an individual image frame and remove the anomalies therein. Because of this the filter 22 of the invention does not require large amounts of memory storage and can operate in real or near real time processing each subsequent image frame as it is received from a sensor.

The filter 22 of the invention can be implemented in a variety of apparatus. These include a strictly hardware device hard wired with appropriate circuits to execute the filtering process steps of the invention or a hardware device having a ROM memory attached thereto containing the coded steps as, for instance, in micocode. Alternately they include a software implementation in an appropriate computer device wherein the instruction steps for operating the filter of the invention are in software and are implemented within the computer CPU with the image frames being I/O'ed (input/output) through conventional I/O ports and the like of the computer.

In order to further the understanding of certain details of the invention a discussion of certain generalized concepts will facilitate the understanding of more specific concepts of the invention. If one considers an individual frame, i.e. an image frame, to be made of pixels or pels which are arranged in rows and columns in the picture frame, an individual pixel or pel, i.e. a picture element, can be identified by its value and its row and column position. The image in the image frame can be constructed by assigning gray values as, for instance, an eight bit value in the range from zero to 255 to each picture element. Thus, if such a image frame was displayed on a CRT, an overall scene would be displayed in black, gray and white as determined by the gray values of the individual picture elements.

An individual picture element can thus be identified by its value P and its position in the image frame by its row coordinate i and its column coordinate j. Thus an ideal individual picture element P at coordinates i, j is identified as $P_{i,j}$. What is received from a sensor as, for instance the sensor 20, however, is not such an ideal or perfect picture element but, in fact, is an observed element $P'_{i,j}$.

This observed picture element $P'_{i,j}$ can be related to the ideal picture element as, for instance, $$P'_{i,j} = a_i P_{i,j} + b_i + \epsilon_{i,j} \qquad \text{(Equation 1)}.$$

This relationship states that an observed picture element is related to the ideal picture element by a gain distortion $a_i$ and offset distortion $b_i$ for the picture element row i and by an unexplained noise or variance element $\epsilon_{i,j}$ indicative of both the row and column position of the picture element. Simply stated this indicates that the ideal image is distorted by some linear gain factor $a_i$, an offset factor $b_i$ and a noise factor $\epsilon_{i,j}$.

If the $\epsilon_{i,j}$ terms (the noise or unexplained variance values) are considered to be local, random and uncorrelated, then in constructing a filter of the invention they can be considered as averaging out over an area of the image frame which incorporates a sufficient number of picture elements. If the $\epsilon_{i,j}$ terms are considered to average out, the above relationship between the observed and the ideal picture element can be rearranged as follows:

$$P_{i,j} = a_i^{-1}[P'_{i,j} - b_i] \qquad \text{(Equation 2)}.$$

If however the error term $\epsilon_{i,j}$ is included and it is considered that a restored image would be proportional to this term, than an estimated ideal image $P^*_{i,j}$ is related to the observed image as follows:

$$P^*_{i,j} = a_i^{-1}[P'_{i,j} - b_i] \qquad \text{(Equation 3)}.$$

When $\epsilon_{i,j}$ is not equal to zero, only a determination of the $P^*_{i,j}$, i.e. the estimated value for the picture element, can be made instead of a determination of the ideal picture element $P_{i,j}$. Given an observed image $P'_{i,j}$ it is not possible to determine $a_i$ and $b_i$ without knowledge of the ideal image $P_{i,j}$. However, a determination of an estimate $a^*_i$ and $b^*_i$ can be made.

It has been found that adjacent or neighboring pixel elements in an image are normally very strongly related to each other and non adjacent picture elements tend not to be related.

For the filter of the invention an advantage is taken of the finding that neighboring picture elements are related. By considering the homogeneity of a small neighborhood or small set of related picture elements estimates of the gain $a^*_i$ and the offset $b^*_i$ are possible for restoration of an artifact contaminated image.

If picture elements $P_{i,j}$ and $P_{i+1,j}$ are from a homogeneous region then $$a_i P_{i,j} + b_i = a_{i+1} P_{i+1,j} + b_{i+1} \qquad \text{(Equation 4)}.$$

If this above relationship is rearranged as follows:

$$P_{i,j} \approx \frac{a_{i+1}}{a_i} P_{i+1} + \frac{1}{a_i} (b_{i+1} - b_i), \quad \text{(Equation 5)}$$

it is noted that the picture elements $P_{i,j}$ and $P_{i+1,j}$ are related by a linear multiplicative factor: $a_{i+1}/a_i$ and an additive factor: $(1/a_i)(b_{i+1}-b_i)$.

If this same principle is applied between rows $(i+1)$ and $(i+2)$ a similar relationship:

$$P_{i+1,j} \approx \frac{a_{i+2}}{a_{i+1}} P_{i+2,j} + \frac{1}{a_{i+1}} (b_{i+2} - b_i), \quad \text{(Equation 6)}$$

is noted. In equation 6, as with equation 5, $P_{i+1,j}$ is related to $P_{i+2,j}$ by a linear multiplicative factor: $a_{i+2}/a_{i+1}$, and an additive factor: $(1/a_{i+1})(b_{i+1}-b_{i+1})$.

If the above relationships are combined row i can be related to row $(i+2)$ as follows:

$$\begin{aligned}P_{i,j} &\approx \frac{a_{i+1}}{a_i} \frac{a_{i+2}}{a_{i+1}} P_{i+2,j} + a_{i+1}(b_{i+2} - b_{i+1}) + \\ &\quad \frac{1}{a_i}(b_{i+1} - b_i) \\ &\approx \frac{a_{i+1}}{a_i} \frac{a_{i+2}}{a_{i+1}} P_{i+2,j} + \frac{a_{i+1}}{a_i} \frac{1}{a_{i+1}}(b_{i+2} - b_{i+1}) + \\ &\quad \frac{1}{a_i}(b_{i+1} - b_i)\end{aligned} \quad \text{(Equation 7)}$$

Again it can be noted that correction factors for row $(i+2)$ relative to row i are a linear multiplicative factor:

$$\frac{a_{i+1}}{a_i} \frac{a_{i+2}}{a_{i+1}}$$

that is the product of factors derived using adjacent rows and an additive factor:

$$\frac{a_{i+1}}{a_i} \frac{1}{a_{i+1}}(b_{i+2} - b_{i+1}) + \frac{1}{a_i}(b_{i+1} - b_i)$$

which involves individual additive factors, one which involves individual additive factors, one multiplied by a linear multiplicative factor.

If this process is continued it becomes evident that a linear adjustment for row $(i+k)$ relative to row i is a product of k linear factor with these factors determined by comparing adjacent linear line pairs. It is important however, to remember the above teachings with respect to homogeneity of the image. An arbitrary k row can simply not be compared to row i. The rows must be related such that they essentially contain homogeneous data, that is related data. It has been found that this can be achieved by selecting rows and/or columns which are proximal or adjacent to one another in an image frame since the probability of such proximal rows or columns containing related or homogenous data is high.

Utilizing the above concept a gain correction factor, e.g. the $a_i$ factor above, can be selected if it reflects a linear multiplicative factor. Further an offset correction factor, e.g. the $b_i$ factor above, can be selected if it reflect an additive factor.

If related or homogeneous data is utilized a statistical variance can be selected for a gain correction factor since it incorporates a linear multiplicative factor. In a like manner a statistical mean can be selected as an offset factor since it incorporates an additive adjustment factor. However, this requires that these statistical correlation factors be utilized on picture elements which in fact are related.

This invention utilizes a mask to select related picture elements. For use in the illustrative embodiment herein a mask 38 of FIG. 5 is selected. The mask 38 relates picture element $P_{i,j}$ with respect to both its preceding and post occurrence related elements $P_{i,j-1}$ and $P_{i,j+1}$ respectively in the same row as element $P_{i,j}$ as well as 3 elements in the same column positions in a row displaced two rows previously and 3 elements in the same column positions in a further row displaced three rows previously.

While wishing not to be bound by theory it is believed that by ignoring the picture elements in row $P_{i-1}$ (the immediate preceeding row) and not including them in the mask 38, sensory artifact factors included within the $\epsilon_{i,j}$ term of Equation 1 are lessened since the $\epsilon_{i,j}$ factors tend to be nonhomogeneous and thus do not cancel out with respect to adjacent pixels. Over a larger picture element area however the $\epsilon_{i,j}$ terms tend to be more homogeneous and thus cancel out.

Utilizing the mask 38, the differences between the picture element $P_{i,j}$ and the remaining 8 picture elements in the mask 38 when summed across a row in an image frame can be expressed as a relationship as, for instance, the relationship expressed in the following equation:

$$d_{i,j} = \frac{1}{3} \left[ \sum_{k=j-1}^{j+1} P_{i,k} - \frac{1}{2} \sum_{k=j-1}^{j+1} (P_{i-3,k} + P_{i-2,k}) \right]. \quad \text{Equation 8}$$

Thus across a row $d_{i,j}$ values (the average difference between the picture element $P_{i,j}$ and the eight other respective picture elements includes in the mask 38) are summed. These represent the differences between row i and rows $(i-2)$ and $(i-3)$ for the picture elements in those rows as determined utilizing the mask 38.

For the filter of the invention, a picture element correlation collection step as for instance, the masking analysis step of equation 8, is utilized. Equation 8 in the form listed is used when horizontal anomalies such as the horizontal streaks 36 are to be filtered out of an image frame. If vertical anomalies or vertical streaks are to be filtered, of course, the mask 38 would be passed along the columns of the image frame with an appropriate substitution made in the mask analysis equation (and the hardware or software corresponding to it or utilized to implement it) to reflect that the mask is processed across the columns and incremented or stepped along each row during the column processing.

In essence the filter step as implemented by Equation 8 (or an equilivent equation as for instance an equation for moving a mask verticially) measures and collects the difference in gain between succeeding columns in the image frame as analyzed utilizing the mask 38. The mask 38 after stepping across a first set of rows in the image frame is then incremented down to step across a next set of image rows. That is, the mask 38 is first oriented on $P_{i,j}$ measuring the picture elements in row $P_{i,j}$ and $P_{i-2,j}$ and $P_{i-3,j}$ as it is stepped across these rows and then is incremented to row $P_{i+1,j}$ and stepped across this row measuring the picture elements in rows $P_{i+1,j}$, $P_{i-1,j}$ and $P_{i-2,j}$.

Put in other terms the mask is swept across the image frame and picture elements in row 4 are compared to rows 1 and 2. The mask is then incremented one row to orient it on row 5 and row 5 is then compared to rows 2 and 3. The mask is then further incremented one row and row 6 is compared to rows 3 and 4. This is done for the totality of the image frame.

In progressing the mask 38 across the image frame, stepping across as, for instance, row 4, data for picture elements in rows 1 and 2 is utilized for comparing the picture elements of row 4. Since it is only at row 4 that there are three previous rows, i.e. rows 1, 2 and 3, the mask 38 cannot be used for the first three rows in the same manner as it is used for the remainder of the rows, however, normally there is a border on any image frame which mitigates this difference. This border can essentially be ignored since generally in sweeping across an environment setting targets or other items of interest in that setting tend to become centered in the image frame.

As a practical expedient border columns can be purposely ignored on both the left and right hand side of the image. Further as is the case for an implementation of the invention described below, the picture elements of the upper border of the image of the frame image can be assume to have ideal gain values i.e. a value of 1. The lower border could also be treated in a similar manner. In sweeping an image, a sensor tends to have more distorted data on the edges of the image than in the center of the image and thus ignoring of the borders of an image results in loss of little or no meaningful image data.

In order to utilized Equation 8, for row 4, data for the picture elements in rows 1,2 and 3 are processed but are not used directly in the calculations of adjustments for the remainder of the rows.

If it is desired to correct the picture elements in the totality of an image frame, a first sweep of a mask, such as a mask 38 can be made in a top down manner which results in obtaining complete data for the bottom rows and a second sweep can be made in a bottom up manner resulting in obtaining complete data for the top rows.

The above correlation parameter collection process can be enhanced by taking into account the average differences of the picture elements across an image row. Thus, after obtaining each of the individual differences between the picture elements of a row with the mask 38, the average difference $\bar{d}_i$ can be calculated as, for instance, using Equation 9 or an equilivent method as follows:

$$d_i = \frac{1}{m} \sum_{j=1}^{m} d_{i,j}$$ Equation 9

In further computations the individual differences $d_{i,j}$ are then all made relative to the average difference by substracting the average difference $\bar{d}_i$ from them.

While neighboring picture elements in an image frame tend to be very homogeneous, when an object is encountered in that image frame the homogeneity of the neighboring elements decreases. In FIG. 6, in processing the mask 38 across row i comparing the picture elements in row i to those of row i−2 and row i−3, at row i, column x+1 the mask 38 encounters a real object 40.

Real object 40 is not an anomaly but in fact is an object or target within the field of view being scanned. Picture elements in row i upto and including column x tend to be homogeneous with respect to picture elements in rows i−2 and i−3 upto and including column x, however those in column x+1 do not because at this point the mask 38 has encountered the object 40.

By incorporating picture elements in row i, column x+1, in the difference determinations as expressed in Equations 8 (with or without utilizing the average row correction factor of equation 9), an effect of the real new object 40 would distort the correction factors being determined for removal of the anomalous streaking artifacts. This, however, can be corrected for by setting a threshold and only utilizing those difference parameters $d_{i,j}$ which are within or bounded by the threshold. Those difference parameters as, for instance ones occurring because of the presence of the real object 40 in row i, column (x+1) of FIG. 6, which are not within the bounds of the threshold, that is they are extrinsic of the threshold, will clipped about the threshold and will not be utilized further.

FIG. 8 shows a histogram of a sweep across a scene as for instance across the row i of FIG. 6. The majority of the picture elements fall in the major area 42 of the histogram clustered about the average deviation $\bar{d}_i$. However, those picture elements which occur because of the appearance of the object 40 in the scene of FIG. 6 fall into the area 44 of the histogram.

A threshold value $t_i$ can be chosen such that only those $d_{i,j}$ values which lie in the area 42 which is less than the absolute value of the threshold chosen are further processed. As such the threshold essentially clips or eliminates from consideration or filtering purposes those picture elements which occur in local non-homogeneous neighborhoods as the result of the appearance of a real object. Since real objects destroy the homogeneity of a local neighborhood, sets of picture elements which include the picture elements from the real object are clipped and are not used for further correction parameter determinations.

Normally the object size of any real objects in an image frame are sufficiently small compared to the overall size of the frame itself that any real object is encountered in sweeping across a row or a column for only a portion of that row or column. This is evident in FIG. 6 for the object 40. To eliminate the real objects, the threshold cutoff value can be chosen arbitrarily, however, for typical image frames a threshold cutoff value of 20% is normally sufficient to eliminate any effect of real objects during correction of the image frame to remove anomalous artifacts. Depending upon the image frames one might select threshold values of from about 0% to about 75% or typically at from about 5% to about 50%. Thus if very small objects are expected within an image frame lower threshold values would be selected and if large objects are expected within an image frame larger threshold values would be selected.

While it is theoretically possible as is seen in FIG. 7 that a real object 46 will extend in a perfect straight line across the field of view of an image frame parallel to a frame edge, for all practical purposes such large real objects such as the object 46 will either not have perfectly sharp edges or will not have edges which are parallel to one of either the vertical or horizontal axis or both. Thus the probability of encountering such a real object 46 within an image frame is very low. Because of this the probability of such a real object 46 distorting the collection of correlation parameters is also low.

After the difference values $d_{i,j}$ are obtained by processing the mask 38 completely over the image frame, means and variances of the collected $d_{i,j}$'s can be determined as, for instance, using the following equation 10 for the mean and equation 11 for the variance. The $d_{i,j}$'s are made relative to the overall characteristics of the image row by making each $d_{i,j}$ relative to the overall row by substracting the average difference $\bar{d}_i$ from each individual $d_{i,j}$ prior to summation and threshold processing as per equations 10 and 11.

$$\mu_{ki} = \frac{1}{n(1-\text{perot})} \sum_{j \ |d_{i,j}| < t_i} (p_{i-k,j}) \quad \text{Equation 10}$$

$$\sigma_{ki}^2 = \frac{1}{n(1-\text{perot})} \sum_{j \ |d_{i,j}| < t_i} p_{i-k,j}^2 - \quad \text{Equation 11}$$

$$\frac{\left( \sum_{j \ |d_{i,j}| < t_i} p_{i-k,j} \right)^2}{n(1-\text{perot})}$$

Equations 10 and 11 and the process steps they represent take into account the utilization of a percentage threshold 'perot' to eliminate the effect of real objects being included in collecting the parameters which are used to eliminate sensor induced artifacts. In Equations 10 and 11 the differences for the picture elements P are summed across the image frame for only those elements whose absolute value is less than a selected threshold $t_i$.

The percentage threshold 'perot' is globally utilized over the totality of the image frame to eliminate the effect of any real object in calculating the means and variances for use in making $a_i^*$ and $b_i^*$ parameter estimations. Thus, only picture elements as, for instance picture elements in major area 42 which are not part of a real object are utilized in calculating the correlation parameters, i.e the means $\mu$ and variances $\sigma^2$.

Referring for a moment to FIGS. 9 and 10, an image frame is received from a sensor element or other system component as a digital serial data stream and is temporarily stored in a buffer 48. A mask is processed sequentially across rows of the image. The rows are stepwise or otherwise retrieved from the buffer 48 during this process and certain correlation parameters are collected. These correlation parameters are generated in the correlation collection step indicated at 50 of FIG. 9, which is also shown and expanded at 50 of FIG. 10 to indicate more detailed steps in FIG. 10.

In FIG. 10 the correlation collection step indicated at 50, is broken down into the steps of collecting the differences $d_{i,j}$ along each row at 52, determining the average $\bar{d}_i$ along each row at 54, creating a histogram of $d_{i,j}-\bar{d}_i$ for each row at 56, clipping the histogram at a threshold $t_i$ at 58 followed at 60 by determining the means, $\mu$, and variances, $\sigma^2$ in each row for all pixel elements wherein the absolute value of the difference of $d_{i,j}$ is below the threshold $t_i$.

For use in implementing the filter 22 of the invention, as noted above, the picture elements of the image frame can be stored in a suitable buffer 48 as, for instance a two dimensional array and the remainder of the computational data can be stored in temporary and refreshable buffers as, for instance one dimensional arrays.

Figure 11:
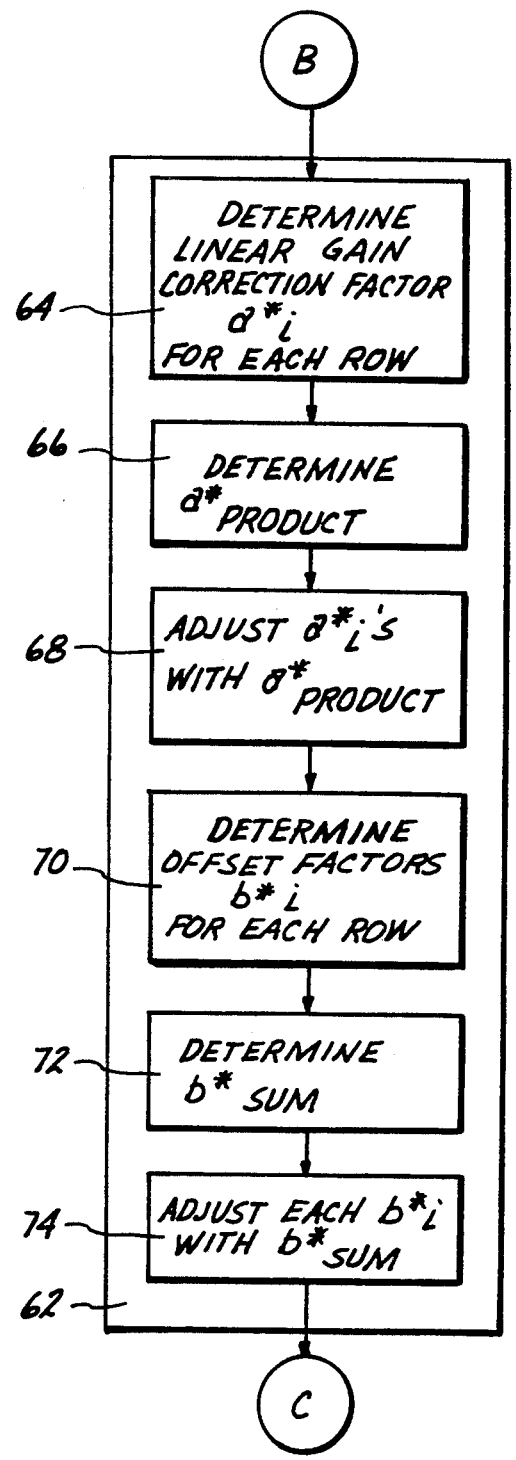

The data now generated in the correlation collection step at 50 is now utilized in a correction parameter determining step shown both at 62 in FIG. 9 and in an expanded form also at 62 in FIG. 11. Estimates for the gains $a_i^*$ are obtained utilizing Equation 12 for the mask 38.

$$a_i^* = \sqrt{\frac{a_{i-3}^* \sigma_{3i}^2 + a_{i-2}^* \sigma_{2i}^2}{2\sigma_{0i}^2}} \quad \text{Equation 12}$$

It is of course, realized that if a different mask was utilized an appropriate equation equivalent to Equation 12 would be utilized to mimic the mask parameters. In any event, the normalized standard deviations of the variances across the rows which represent linear multiplicative factors are utilized to obtain an estimated value $a_i^*$ of a gain correction parameter. This is identified at 64 in FIG. 11.

As is evident from Equation 12 the derivation of the linear gain correction factor of each subsequent row includes the previously determined linear gain factors of previous rows. In order to insure that the overall gain of the image across the entirety or totality of the image frame does not change because of progressively incorporating increases in gain between subsequent rows, the product of all the $a_i^*$ is determined in a suitable manner as, for instance equation 13, and then each individual $a_i^*$ is adjusted by a factor of the product as per Equation 14.

$$a^*_{prod} = \prod_{i=1}^{n} a^*_i \quad \text{Equation 13}$$

$$a^*_i = \frac{a^*_i}{\sqrt[n]{a^*_{prod}}} \quad \text{Equation 14}$$

In reference to FIG. 11, at 66 the $a^*$ sub product as is exemplified by Equation 13 is determined and at 68 the $a^*_i$'s are adjusted with this product as per Equation 14.

Estimates for the offset correction factors $b_i^*$ are also obtained in a suitable manner as, for instance as follows:

$$b^*_i = \frac{1}{2}[\mu_3 \ _i a^*_{i-3} + b^*_{i-3} + \mu_2 \ _i a^*_{i-2} + b^*_{i-2}] - \mu_0$$
$$ia^*_i \qquad \text{Equation 15.}$$

As discussed generally above, correction offset factors can be estimated utilizing a procedure which takes into the account the linear multiplicative factor and individual additive factors as generally discussed with respect to Equations 6 and 7 above.

The offset factors are determined at 70 in FIG. 11 utilizing Equation 15. However, again in order to insure that the overall bias of the image does not change across the image frame, the overall mean of the image offset adjustment, i.e. the $b^*_{sum}$, is determined in a suitable manner as, for instance utilizing Equation 16 at 72. Then each of the $b^*_i$'s can be adjusted with the $b^*_{sum}$ in a suitable manner as, for instance utilizing Equation 17 at 74 in FIG. 11.

$$b^*_{sum} = \sum_{i=1}^{n} [\mu_0(a^*_i - 1) + b^*_i] \quad \text{Equation 16}$$

$$b^*_i = b^*_i - \frac{b^*_{sum}}{n} \quad \text{Equation 17}$$

It has been found that generally the offset factor has a greater effect on decreasing sensory artifacts than the gain factor. Generally, the gain factors, the $a^*_i$ are very close to unity (1). Utilizing these findings other suitable correction parameter determinations as for instance the processes exemplified by Equations 18 and 19 can be substituted as alternates for Equations 16 and 17.

$$b^*_{sum} = \sum_{i=1}^{n} b^*_i \quad \text{Equation 18}$$

$$b^*_i = b^*_i - \frac{b^*_{sum}}{n} \quad \text{Equation 19}$$

These alternate correction parameter determinations differ from Equations 16 and 17 in that they take into account the finding that the general mean of a particular line in certain instance would be very close to 1 and the linear factors can therefore be essentially ignored. However, for greater accuracy in correcting and removing sensory artifacts in an image frame, preferredly the linear factors would be taken into account when making the offset corrections.

Referring now to FIGS. 9 and 12, once the correction parameters have been determined image correction as shown at 76 in FIGS. 9 and 12 can be effected. In image correction at 76 in FIG. 12 computed correction parameters from 62 of FIG. 11 are utilized at 78 to adjust the picture elements of the image frame stored at 48 to produce the corrected image frame picture elements. The corrected image frame picture elements can then be clipped to a range as, for instance, to an 8 bit gray scale range of 0 to 255 in range clipper 80.

The correction step at 78 is shown in Equation 20 wherein the adjusted picture element $P^*_{i,j}$ is determined from the observed picture element $P'_{i,j}$ by multiplying it by the gain factor $a^*_i$ and adding to it the offset factor $b^*_i$ as follows:

$$P^*_{i,j} = a^*_i P'_{i,j} + b^*_i \quad \text{Eqaution 20}$$

As per the process described in FIG. 9, an image frame has been corrected utilizing a filter 22 of the invention to remove horizontal sensory artifacts, i.e. streaks which were introduced into the image frame as anomalous data by the sensor 20. Depending upon the sensors utilized and the desired degree of correction necessary for a particular image frame, one or more image corrections will be effected. As per FIG. 2 a horizontal filter 82 as per the filter described in discussing the apparatus and process of FIG. 9 and the related figures, has been utilized to remove horizontal streaking from an image.

The output from the horizontal filter 82 could be utilized directly as an adjusted image or alternatively it could serve as input data to a vertical filter 84. In the vertical filter 84, the image data would be processed in a manner equivalent to that seen above for the horizontal processing except that vertical anomalies would be removed from the image. This image could then be utilized as an adjusted image or the image could be processed even further by passing it through a further horizontal filter 86 and a further vertical filter 88.

Since the filters of the invention process or filter the images utilizing only one image frame at a time and do not require either a proceding or subsequent image frame to effect this filtering process, as noted above they operate in real time or near real time. For a sequentially filtering process as is depicted in FIG. 2, individual image frames could be pipelined through the successive filter stages, that is from filter 82 to filter 84 to filter 86 to filter 88 etc., also in real or near real time.

Since each image frame is filtered independent of any other image frame, the serial filters of FIG. 2 operating in a pipeline can independently operate on successive image frames in an expedient manner. No one of the filters 82, 84, 86 or 88 is depending upon any of the other of the filters or the image frame currently being processed in the other filters.

A device of the invention is illustrated in FIG. 13. Digitized data from a sensor 90 is stored in frame store 92. Mask device 94 processes the store picture elements. Output from mask device 94 is processed to obtain the average deviation of each frame row by device 96 and the output of this device and that of device 94 are fed to device 98 to obtain relative picture element deviations. A threshold cut off and the output of device 98 are input to device 100 for creating a histogram of this input data. Device 102 determines the threshold cut off in the data and device 104 process the data for the means and variances of the differences of the picture elements in the image rows.

The row difference values in storage arrays 106 are processed in multipliers 108 and 110 with the respective variances from device 104. The output of the multipliers 108 and 110 is fed to device 112 for summing the two sets of data and this is output to divider 114 for division by the variance of the test row. The root of the output from the divider 114 is processed in root device 116 with the output of this device stored in the storage arrays 106 of a gain storage buffer 118.

The adjusted data in storage arrays 106 is also fed to multipliers 120, 122 and 124 for processing with respective means from device 104. Unadjusted data in storage arrays 126 are combined with the output from the multipliers 120, 122 and 124 in device 128. Device 128 outputs uncorrected (corrected for the total frame) offsets to storage arrays 126 of an offset storage buffer 130.

Mean data and mean data processed with data from storage array 106 in multiplier 124 is combined with data from buffer 130 and feed back data in device 132 and the output of this device is accumulated in accumulator 134. The uncorrected offset data is corrected with the output from device 134 in device 136.

Original picture element data in buffer 92 is processed with data from the gain buffer 118 in multiplier 138 and the output of this in turn is processed with the output from device 136 in picture element correction device 140. The output from the correction device 140 is fed to limiter 142 for clipping the corrected image frame picture element to a particular gray scale. A filtered frame image is output from the limiter 142.

The device of FIG. 13 does not adjust the gain correction parameters for the totality of the picture frame as is illustrated in the process steps 66 and 68 of FIG. 11, however, if desired these steps could be implemented in the the device of FIG. 13. The correction for the offsets over the totality of the image frame corresponding to steps 72 and 74 of FIG. 11 are however implemented in the device of FIG. 13 in devices 132, 134 and 136.

In FIG. 14 a detailed flow diagram is shown detailing an implemention of a filter of the invention. A histogram cutoff value is obtained at input 144. The first four rows of an image frame are then processed at loop 146. These first four rows are read into a storage array at row store 148 and loop variables are zeroed out at 150. Loop 152 is then iterated reading across the columns and the sums and the sums$^2$ of the picture elements of the first four rows are then determined at 154. These sums and sums² are then utilized to compute the means and variances for the first four rows at 156.

The remainder of the rows of the picture elements starting at row 4 are then processed in loop 158. A row is stored into the array storage element at 160 and variables zeroed out at 162. Nested loops 164 and 166 are then iterated to get the mask picture elements at 168. The differences $d_{i,j}$ are calculated at 170 and the overall sum of each row $d_i$ are calculated at 172.

Average differences for each row are then computed at 174. Variables are zeroed out and the histogram bin size is set or reset at 176. The columns are read at loop 178 and the pixel differences are made relative to the average difference at 180. The appropriate histogram bin for the pixel is selected at 182 and the histogram bin is incremented at 184.

The histogram bin cutoff is then evaluated with respect to the filled histogram bin at decisions 186a and 186b and if it is inappropriate with respect to the histogram (186a) and if the maximum bin size has not been reached (186b), the bin is incremented at 188. If the histogram is within the bin size or the maximum bin size has already been reached, the process continues wherein the largest histogram bin is selected. Threshold cutoff is set at 190 and the sum and sum² counters are zeroed at 192.

Loop 194 is iterated and the relative differences $d_{i,j}$ are examined to see if they fall within the histogram cutoff range at decision 196. If the relative differences fall within the histogram range then sums and sum² are determined at step 198. If the differences are outside of the histogram range the loop is iterated and these values are ignored. For those values within the histogram range the values are then utilized to compute the means and variances at 200 for the fourth row through the maximum row.

The above steps correspond to processing step 50 of FIG. 9 as was detailed in FIG. 11 at 52 through 60 respectively.

Having determined the correlation parameters for the image frame, loop 202 is now iterated and the a* value for the top rows of the image frame which were not analyzed with the mask is set to 1 at 204. Gain parameters are set at 206 and the loop 208 executed. Within the loop 208 the a* for rows 4 through the maximum row are computed at 210. The parameters are zeroed at 212 and loop 214 executed. In loop 214 the a* product for rows 4 through the maximum row is found at 216. A computed gain multiplier is then calculated at 218 and range variables are set at 220.

A loop 222 is executed and the $a^*_i$ values are adjusted for the total gain of the image frame at 224. Range parameters are set at 226 and a loop 228 executed wherein the b* parameters are zeroed for rows 1 through 3 at 230.

A loop 232 is executed and the b*'s for rows 3 through the maximum row are computed at 234. At 236 range parameters are set and loop 238 is then executed wherein the b* sum is computed at 240. The mean of the sums is computed at 242 followed by setting range parameters at 244. A loop 246 is executed and computed adjusted b* offset parameters are calculated at 248.

The above referred to steps 202 through 248 correspond to the process steps of FIG. 9 indicated at 62 as detailed in FIG. 11 at 64 through 74 respectively.

After calculating the correction parameters for the totality of the image frame, nested loops 250 and 252 are iterated and the picture elements adjusted with the correction parameters at 254. The adjusted picture elements are then clip at step 256 between 0 and 255 to remain within the gray scale of the image frame. A corrected image frame is then output at 260 for further use as, for instance, by the global processor 24 of FIG. 1 or for display storage or other process depending upon the implementation which the filter of the invention is being utilized for.

As noted the filter of the invention can reside in hardware and can utilize an appropriate micro code or the like for implementing the hardware filter or alternately it can be utilized utilizing a CPU which processes image frames from tape input, other memory input or from direct input from an appropriate sensor under the control of software.

An implementation of the filter of the invention is given as a Fortran language program which corresponds to the flow diagram of FIG. 14. Certain more trivial routines of this code have been left out for brevity of the code as, for instance, filling arrays and the like and I/O (input/output) routines which would be device dependent. This code is as follows.

```
C                    CORRELATION PARAMETERS
C                     (STATISTIC COLLECTION)

PARAMETER    (MAXR=380,MAXC=512,NROWR=4)

INTEGER*4    ISUM0,ISUM2,ISUM3,ISMSQ0,ISMSQ2,ISMWQ3
      INGEGER*4    IPREC0,IPREC2,IPREC3

DIMENSION    IMG(MAXC,NROWR)
      DIMENSION    IHIST(0:192),SDIFF(MAXC)
      DIMENSION    RMEAN0(MAXR),RMEAN2(MAXR),RMEAN3(MARX)
      DIMENSION    VAR0(MAXR),VAR2(MAXR),VAR3(MAXR)
      DIMENSION    ICUTS(MAXR)

C  FORTRAN INTRINSIC FUNCTIONS USED HERE ARE WELL-KNOWN FORTRAN
C  STANDARDS:
C  IIMOD - MODULUS FUNCTION, EXAMPLE IIMOD(10,3) IS 1
C  IIFIX - REAL TO INTEGER CONVERSION
```

```
C   FLOAT - INTEGER TO REAL CONVERSION
C   IMAXO - MAXIMUM OF TWO INTEGERS
C   IMINO - MINIMUM OF TWO INTEGERS
C   IIABS - ABSOLUTE VALUE OF AN INTEGER
C   USER ENTERS TAIL PERCENTAGES - PEROT, DEFAULT OF 20%

PEROT=20.0
        TYPE 611
611     FORMAT(' ENTER TAIL PERCENT DIFFERENCE TO INORE - ',$)
        ACCEPT *,PEROT
        NPEROT=(PEROT*(MAXC-10))/100.0
C
C   READ (INPUT) AND PROCESS TOP 3 LINES. THESE LINES ARE NOT
C   AS DIRECTLY INOVLVED IN THE ADJUSTMENT CALCULATIONS,
C   THEREFORE, THE FILTER SHOULD NOT BE AS SENSITIVE TO BAD
C   IMAGE LINES AT THE TOP

DO 10 JR=1,NROWR   ! THIS LOOP IS JUST FOR TOP LINES OF
C                                         AN IMAGE

C   STARTING AT IMG(A,IMAXO(1,JR-1))
C   READ THE JR TH LINE OF IMAGE INTQ ARRAY IMG(    )
C   (THE EXACT CODE IS ELIMINATED FOR SIMPLICITY.)

...

IF(JR.EQ.1) THEN

C     THE FIRST LINE OF THE IMAGE IS MERELY A HEADER LINE
C     CONTAINING NO VALID IMAGE DATA
        ELSE
                ISUM0=0.0
                ISMSQ0=0.0
                DO 1 J=1,MAXC
                IPREC0=IMG(J,JR-1)          !TO GET *4 ARITHMETIC
                ISUM=ISUM0+PREC0
                ISMSQ0=ISMSQ0+IPREC0**2
11              CONTINUE

C     COMPUTE MEAN AN VARIANCE OF TOP LINES OF THE IMAGE

RMEAN0(JR-1)=FLOATJ(ISUMO)/MAXC
                RMEAN2(JR-1)=RMEAN0(JR-1)
                RMEAN3(JR-1)=VAR0(JR-1)

VAR0(JR-1)=FLOATJ(ISUM0)/MAXC
                VAR2(JR-1)=VAR0(JR-1)
                VAR3(JR-1)=VAR0(JR-1)

END IF

10      CONTINUE

C   $$$   MAIN LOOP   $$$

C   THIS LOOP IS FOR ALL OTHER LINES (ROWS) OF THE IMAGE
```

```
      DO 20 MANR=NROWR,MAXR
      IADD0=IMOD(MANR-1,NROWR)+1      !THE MODULUS FUNCTIONS
      IADD2=IMOD(MANR+1-NROWR,NROWR)+1 !MINIMIZE STORAGE
      IADD3=IMOD(MANR-NROWR,NROWR)+1  !REQUIRED FOR IMAGE
                                      ! LINES

C     STARTING AT IMG(1,IADD0)
C     READ THE MANR TH LINE OF IMAGE INTO ARRAY (   )
C     (THE EXACT CODE IS ELIMINATED FOR SIMPLICITY.)

...

C     FIND SMOOTHED DIFFERENCE BETWEEN NEW LINE AND PREVIOUS
C     LINES NOTE: IN THIS VERSION OF THE FILTER, THE LIES ARE NOT
C     MODIFIED IN STORAGE

SUMDIF=0
      DO 25 J=6,(MAXC-5)   !STILL IGNORE BORDER PIXELS AT THE
                           !BEGINNING AND ENDS OF THE LINE
      SDIFF(J)=0
      DO 26 J1=J-1,J+1
      SDIFF(J)=SDIFF(J)+(IMG(J1,IADD3)+IMG(J1,IADD2))/2.0
     1        -IMG(J1,IADD0)      !TOP TWO MINUS BOTTOM
 26   CONTINUE
      SDIFF(J)=SDIFF(J)/3.0
      SUMDIF=SUMDIF+SUMDIF+SDIFF(J)
 25   CONTINUE
      AVGDIF=SUMDIF/(MAXC-10.0)

C     AS OPTIONS FOR COMPUTATIONAL SPEEDUP FOR ABOVE:
C     1. /2.0 DIVISIONS COULD BE DONE BY SHIFTS
C     2. a 1,2,1 KERNEL WEIGHTING WOULD CHANGE A /3.0 DIVISION TO
C     /4.0 ZERO OUT THE HISTOGRAM BINS FOR DIFFERENCES. ACTUALLY
C     DIFFERENCES GENERALLY STAY NEAR ZERO, SO IN THIS CASE, ALL
C     POSSIBLE 256 ARE NOT USED FOR COMPUTATIONAL SPEEDUP.  STUDY
C     ON OUR IMAGERY SHOWED THAT 48 BINS WERE ADEQUATE FOR ALL OF
C     SOME 500 IMAGES

NUMBNS=48                      !VARIABLE NUMBER OF BINS
 35   DO 27 ID=0,NUMBNS
 27   IHIST(ID)=0

C     COMPUTE THE HISTOGRAM OF ABSOLUTE-VALUED DIFFERENCES

DO 28 J=6, (MAXC-5)
                !NOTE:  IIFIX(-0.5=0
      SDIFF(J)=SDIFF(J)-AVGDIF    !SDIFF IS AVGDIF-RELATIVE NOW
      IBIN=(IMIN0(NUMBNS,IIABS(IIFIX(SDIFF(J)))))
      IHIST(IBIN)=IHIST(IBIN)+1
 28   CONTINUE

C     FIND CUTOFF (JUST LESS THAN "20%")

IF(IHIST(NUMBNS).GT.NPEROT) THEN
        TYPE 612
 612    FORMAT (' WARNING ** DIFFERENCE HISTOGRAM RANGE
      OVERFLOW')
      IF(NUMBNS.GE.192)  GO TO 36!MAXED OUT ALREADY
```

```
            NUMBNS=NUMBNS*2          !DOUBLE NUMBER OF HISTOGRAM
                                     !BINS AND TRY AGAIN
            GO TO 35
      END IF

C     FIND THE BIN CORRESPONDING TO THE PEROT CUTOFF

36    IOUT=0
      DO 29 JB=NUMBNS,1,-1
      IOUT=IOUT+IHIST(JB)
      IF(IOUT.GT.NPEROT)  TO TO 31
29    CONTINUE
31    ICUT=JB
      ICUTS(MANR)=ICUT           !SAVE OF ANALYSIS ONLY

C     CHANGE DEPENDS ON LOP-SIDED HISTOGRAM EXCEPT IN VARIANCE
C     FIND MEANS AND VARIANCES OF SMOOTHED IMAGE LINES
C
C     FIND NEW MEAN DIFFERENCE USING JUST THOSE SAMPLES WITH
C     ABSOLUE DIFFERENCES BELOW THE THRESHOLD

NUMIN=0
      ISUM0=0
      ISUM2=0
      ISUM3=0
      ISMSQ0=0
      ISMSQ2=0
      ISMSQ3=0
      DO 33 JC=6,(MAXC-5)
      IF(IIABS(IIFIX(SDIFF(JC))).GT.ICUT) GO TO 33
                                              !DON'T INCLUDE
      NUMIN=NUMIN+1
      IPREC0=IMG(JC,IADD0)       !CONVERT TO INTEGER*4
      IPREC2=IMG(JC,IADD2)
      IPREC3=IMG(JC,IADD3)
      ISUM0=ISUM0+IPREC0             !COMPUTE SUM AND SUM-OF-SQUARES
      ISUM2=ISUM2+IPREC2
      ISUM3=ISUM3+IPREC3
      ISMSQ0=ISMSQ0+IPREC0**2
      ISMSQ2=ISMSQ2+IPREC2**2
      ISMSQ3=ISMSQ3+IPREC3**2
33    CONTINUE
      RNUMIN=NUMIN
      RMEAN0(MANR)=ISUM0/RNUMIN         !CALCULATE MEANS AND
                                        !VARIANCES
      RMEAN2(MANR)=ISUM2/RNUMIN
      RMEAN3(MANR)=ISUM3/RNUMIN
      VAR0(MANR)=((ISMSQ0-ISUM0*RMEAN0(MANR))/RNUMIN)
      VAR2(MANR)=((ISMSQ2-ISUM2*RMEAN2(MANR))/RNUMIN)
      VAR3(MANR)=((ISMSQ3-ISUM3*RMEAN3(MANR))/RNUMIN)
20    CONTINUE

C                CORRECTION PARAMETER DETERMINATION

DIMENSION    SADJ1(MAXR),SMADJ1(MAXR)     !ANALYSIS STORAGE
      REAL         MEADJ(MAXR),ADJ(MAXR)
      DIMENSION    RMEAN0(MAXR),RMEAN2(MAXR),RMEAN3(MAXR)
```

```
      DIMENSION   VAR(MAXR),VAR2(MAXR),VAR3(MAXR)
      DOUBLE PREVISION DSUM,DTIME,DSUMMX,DSUMMN

C     COMPUTE LINEAR MULTIPLIER FACTORS
      DO 49 J=1,NROWR-1
      ADJ(J)=1.0       !TOP LINES, NO ADJUST
49    SADJ1(J)=ADJ(J)
      SMNAJ1=100.0
      SMXAJ1=-100.0
      DO 51 JR=NROWR,MAXR
      JR2=(JR+2)-NROWR
      JR3=(JR+1)-NROWR
      ADJ(JR)=SQRT(((VAR3(JR)*ADJ(JR3)+VAR2(JR)*ADJ(JR2))/2.0)/
     1  VAR0(JR))
      SADJ1(JR)=ADJ(JR)       !SAVE FOR ANALYSIS
      SMNAJ1=AMIN1(SMNAJ1,ADJ(JR))     !ALSO RANGE
      SMXAJ1=AMAX1(SMXAJ1,ADJ(JR))

51    CONTINUE

C     FIND PRODUCT OF ADJ'S USING LOGS, SIMPLY MULTIPLYING THESE
C     VALUES WOULD CAUSE A LOSS OF PRECISION.  THIS IS ALL DONE IN
C     DOUBLE PRECISION

DSUM=0.0
      DSUMMN=0.0
      DSUMMX=0.0
      DO 52 JR=NROWR,MAXR
      DSUM=DSUM+DLOG(DBLE(ADJ(JR)))
      DSUMMN=DMIN1(DSUMMN,DSUM)        !SAVE RANGE OF RUNNING
      DSUMMX=DMAX1(DSUMMN,DSUM)        !LOG PRODUCT FOR ANALYSIS
52    CONTINUE

PVAR=SNGL(1.0/DEXP(DSUM/FLOATI(MAXR)))

C     ADJUST ALL LINEAR ADJUSTMENT PARAMETERS, ADJ, BY DIVIDING BY
C     THE PRODUCT TO INSURE THE OVERALL GAIN OF THE IMGE REMAINS
C     APPROXIMATELY CONSTANT.  THIS MAY NOT ALWAYS BE NECESSARY,
C     BUT IT IS A GOOD IDEA.

SMNAJ2=100.0
      SMXAJ2=-100.0
      DO 53 JR=1,MAXR
      ADJ(JR)=ADJ(JR)*PVAR
      SMNAJ2=AMIN1(SMNAJ2,ADJ(JR))
      SMXAJ2=AMAX1(SMXAJ2,ADJ(JR))
53    CONTINUE

C     NOW ADJUST MEANS
C     THERE MAY BE SOME TYPE OF ITERATIVE APPROACH TO THESE TWO
C     LOOPS BUT I DON'T THINK IT EFFICIENT

SMNMJ1=10000.0
      SMXMJ1=-10000.0
      DO 54 J=1,NROWR-1                INITIALIZE THEM TO 0

54    MEANDJ(J)=0.0
      DO 55 JR=NROWR,MAXR
```

```
      JR2=(JR+2)-NROWR
      JR3=(JR+1)-NROWR
      MEADJ(JR)=(RMEAN3(JR)*ADJ(JR3)+MEADJ(JR3)
     1          +RMEAN2(JR)*ADJ(JR2)+MEADJ(JR2))/2.0
     2          -RMEAN0(JR)*ADJ(JR)
      SMADJ1(JR)=MEADJ(JR)
      SMNMJ1=AMIN1(SMNMJ1,MEADJ(JR))   !SAVE RANGE FOR ANALYSIS
      SMXMJ1=AMAX1(SMXMJ1,MEADJ(JR))
55    CONTINUE

C     SET SUM OF ADJUSTMENTS TO ONE

SUMEDJ=0.0
      SUMEMN=0.0
      SUMEMX=0.0
      DO 56 JR=NROWR,MAXR
      SUMEDJ=SUMEDJ+((RMEAN0(JR)*ADJ(JR)+MEADJ(JR))-RMEAN0(JR))
      SUMEMN=AMIN1(SUMEMN,SUMEDJ)      !SAVE RUNNING RANGE FOR
      SUMEMX=AMAX1(SUMEMX,SUMEDJ)      !ANALYSIS
56    CONTINUE
      SUMEDJ=SUMEDJ/MAXR               !MEAN OF ADJUSTMENTS
      SMNMJ2=10000.0
      SMXMJ2=-10000.0
      DO 57 JR=1,MAXR
      MEADJ(JR)=MEADJ(JR)-SUMEDJ
      SMNMJ2=AMIN1(SMNMJ2,MEADJ(JR))
      SMXMJ2=AMAX1(SMXMJ2,MEADJ(JR))
57    CONTINUE

C                              IMAGE CORRECTION

PARAMETER  (MAXR=380,MAXC=512,NROWR=4)
      REAL MEADJ(MAXR),ADJ(MAXR)
      DIMENSION IMG(MASC,NROWR)

C     NOW, ADJUST IMAGE

DO 68 MANR=1,MAXR

C     STARTING AT IMG(1,1)
C     READ IMAGE LINE MANR+1 INTO ARRAY
C     (ASSUMING THE FIRST LINE CONTAINS IMAGE HEADER INFORMATION)

DO 60 J2=1,MAXC
      IMG(J2,MANR)=ADJ(MANR)*IMG(J2,1)+MEADJ(MANR)
      IMG(J2,MANR)=IMAX0(0,IMG(J2,1))        !CLIP AT 0 AND 255
      IMG(J2,MANR)=IMIN0(255,IMG(J2,1))      !IS ONLY 8-BITS
60    CONTINUE

68    CONTINUE
```

What is claimed is:

1. A streak removal filtering method for estimating an image of pixels $P_{ij}$ from measured pixel intensity values $P'_{ij}$ in an image frame, comprising, the steps of assuming that pixels in a predetermined region near the pixel $P_{ij}$ are strongly related to each other and to $P'_{ij}$ and that a correction based on $P^*_{ij} = a^*_i P'_{ij} + b^*_i$ can compute streak removal information, where $a^*_i$ is the gain correction, $P'_{ij}$ is the measured intensity of the pixel, $b^*_i$ is an offset correction, and $P^*_{ij}$ is the estimated value of the pixel $P_{ij}$ of the actual image, as corrected;

performing the following steps in a computer:

computing the differences $d_{ij}$ between each pixel in said region and the measured pixel $P'_{ij}$;

thresholding $d_{ij}$ for values lower than predetermined values above which the difference may be assumed to be due to real object changes in the image;

computing the mean and the variance of the intensity values of the pixels $P'_{ij}$ in said region for which $d_{ij}$ is less than said threshold;

averaging the product of the gain corrections and the variances of the pixels preceding the measured pixel, $P'_{ij}$, ratioed by the variance of the immediately adjacent pixels to estimate said gain correction, $a^*_i$;

averaging the corrected pixel values from regions of pixels preceding the measured pixel, $P'_{ij}$, less the computed means pixel intensity value times the gain corrections of the adjacent pixels to determine said offset correction, $b^*_i$;

computing the estimated value $P^*_{ij}$ of the intensity value of $P_{ij}$ by adding the offset $b^*_i$ to the measured intensity $P'_{ij}$ from said relation $P^*_{ij} = a^*_i P'_{ij} + b^*_i$;

processing successive regions of pixels of the image, in seriatim, in accordance with the above steps, to develop a streak corrected image formed from the corrected estimated values of pixels $P^*_{ij}$; and, thereafter outputting said corrected image of said image frame.

2. The method as set forth in claim 1 further including the steps of selecting n gain correction values for n respective regions in said image, ratioing the gain correction value of the present region by the $n^{th}$ root of the product of the n gain corrections.

3. The method as set forth in claim 2 further including the step of:

reducing the offset correction by the average of all offset corrections after correcting the means of each region according to the computed gain corrections.

4. The method as in claim 1 in which said processing step includes masking to define said region of pixels about $P_{ij}$ to consist of $P'_{ik}$, $P'_{i-3,k}$ and $P'_{i-2,k}$ for $k = j-1, j, j+1$.

5. A streak removal filtering method for estimating an image of pixels $P_{ij}$ from measured pixel intensity values $P'_{ij}$ in an image frame, comprising, the steps of assuming that pixels in a predetermined region near the pixel $P_{ij}$ are strongly related to each other and to $P'_{ij}$ and that a correction based on $P^*_{ij} = a^*_i P'_{ij} + b^*_i$ can compute streak removal information where $a^*_i$ is the gain correction, $P'_{ij}$ is the measured intensity of the pixel, $b^*_i$ is an offset correction, and $P^*_{ij}$ is the estimated value of the pixel $P_{ij}$ of the actual image, as corrected, and assuming the gain $a^*_i$ can be set to unity, as an approximation;

performing the following steps in a computer:

computing the differences $d_{ij}$ between each pixel in said region and the measured pixel $P'_{ij}$;

thresholding $d_{ij}$ for values lower than predetermined values above which the difference may be assumed to be due to real object changes in the image;

computing the mean and the variance of the intensity values of the pixels $P'_{ij}$ in said region for which $d_{ij}$ is less than said threshold;

averaging the corrected pixel values from regions of pixels preceding the measured pixel, $P'_{ij}$, less the computed mean pixel intensity value times the corrected gain correction of the adjacent pixels to determine said offset correction, $b^*_i$;

computing the estimated value $P^*_{ij}$ of the intensity value of $P_{ij}$ by adding the offset $b^*_i$ to the measured intensity $P'_{ij}$ from said relation $P^*_{ij} = P'_{ij} + b^*_i$;

processing successive regions of pixels of the image, in seriatim, in accordance with the above steps, to develop a streak corrected image formed from the corrected estimated values of pixels $P^*_{ij}$; and, thereafter outputting said corrected image of said image frame.

6. Apparatus for removing streaks from an image of pixels $P_{ij}$ from measured pixel intensity values $P'_{ij}$ in an image frame by assuming that pixels in a predetermined region near the pixel $P'_{ij}$ are strongly related to each other and to $P_{ij}$ and that a correction based on $P^*_{ij} = a^*_i P'_{ij} + b^*_i$ can compute streak removal information, where $a^*_i$ is the gain correction, $P'_{ij}$ is the measured intensity of the pixel, $b^*_i$ is an offset correction, and $P^*_{ij}$ is the estimated value of the pixel $P_{ij}$ of the actual image, as corrected; comprising means for computing the differences $d_{ij}$ between each pixel in said region and the measured pixel $P'_{ij}$;

means for thresholding $d_{ij}$ for values lower than predetermined values above which the difference may be assumed to be due to real object changes in the image;

means for computing the mean and the variance of the intensity values of the pixels $P'_{ij}$ in said region for which $d_{ij}$ is less than said threshold;

means for averaging the product of the gain corrections and the variances of the pixels preceding the measured pixel, $P'_{ij}$, ratioed by the variance of the immediately adjacent pixels to estimate said gain correction, $a^*_i$;

means for averaging the corrected pixel values from regions of pixels preceding the measured pixel, $P'_{ij}$, less the computed mean pixel intensity value times the corrected gain correction of the present row to determine said offset correction $b^*_i$;

means for computing the estimated value estimate $P^*_{ij}$ of the intensity value of $P_{ij}$ by adding the offset $b^*_i$ to the measured intensity $P'_{ij}$ from said relation $P^*_{ij} = a^*_i P'_{ij} + b^*_i$; and means for processing successive regions of pixels of the image, in seriatim, in accordance with the above steps, to develop a streak corrected image formed from the corrected estimated values of pixels $P^*_{ij}$.

7. An apparatus as in claim 6 further including
means for selecting n gain correction values for the n respective regions in said image,
means for ratioing the gain correction value of the present region by the $n^{th}$ root of the product of the n gain corrections.

8. An apparatus as in claim 7 further including
means for reducing the offset correction by the average of all offset corrections after correcting the means of each region according to the computed gain corrections.

9. An apparatus as in claim 8 further including
a mask for defining said region of pixels about $P_{ij}$ to consist of $P'_{ik}$, $P'_{i-3,k}$ and $P'_{i-2,k}$ for $k=j-1, j, j+1$.

10. Apparatus for removing streaks from an image of pixels $P_{ij}$ from measured pixel intensity values $P'_{ij}$ by assuming that pixels in a predetermined region near the pixel $P_{ij}$ are strongly related to each other and to $P_{ij}$ and that a correction based on $P^*_{ij}=a^*_i P'_{ij}+b^*_i$ can compute streak removal information where $a^*_i$ is the gain correction, $P'_{ij}$ is the measured intensity of the pixel, $b^*_i$ is an offset value, and $P^*_{ij}$ is the estimated value of the pixel $P_{ij}$ of the actual image, as corrected, and assuming the gain $a^*_i$ can be set to unity, as an approximation; comprising, means for computing the differences $d_{ij}$ between each pixel in said region and the measured pixel $P'_{ij}$;

means for thresholding $d_{ij}$ for values lower than predetermined values above which the difference may be assumed to be due to a real object changes in the image;

means for computing the mean and the variance of the intensity values of the pixels $P_{ij}$ in said region for which $d_{ij}$ is less than said threshold;

means for averaging the corrected pixel values from regions of pixels preceding the measured pixel, $P'_{ij}$, less the computed mean pixel intensity value times the gain corrections of the adjacent pixels to determine said offset correction $b^*_i$;

means for computing the corrected estimate $P^*_{ij}$ of the intensity value of $P_{ij}$ from said relation $P^*_{ij}=-P'_{ij}+b^*_i$; and means for processing successive regions of pixels of the image, in seriatim, in accordance with the above means, to develop a streak corrected image formed from the corrected set of pixels $P^*_{ij}$ formed from the corrected estimated value of pixels $P^*_{ij}$.

* * * * *